US011534188B2

(12) United States Patent
Imai et al.

(10) Patent No.: US 11,534,188 B2
(45) Date of Patent: Dec. 27, 2022

(54) MEDICAL DEVICE AND TREATMENT METHOD

(71) Applicant: TERUMO KABUSHIKI KAISHA, Tokyo (JP)

(72) Inventors: Masaomi Imai, Kanagawa (JP); Yuuki Masubuchi, Kanagawa (JP); Takashi Kitaoka, Kanagawa (JP); Takahiro Chida, Kanagawa (JP); Kazuaki Kanamoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 474 days.

(21) Appl. No.: 15/842,427

(22) Filed: Dec. 14, 2017

(65) Prior Publication Data

US 2018/0103971 A1    Apr. 19, 2018

Related U.S. Application Data

(63) Continuation of application No. PCT/JP2016/067622, filed on Jun. 14, 2016.

(30) Foreign Application Priority Data

Jun. 16, 2015 (JP) .............................. JP2015-120973

(51) Int. Cl.
*A61B 17/221* (2006.01)
*A61F 2/01* (2006.01)

(52) U.S. Cl.
CPC ............ *A61B 17/221* (2013.01); *A61F 2/013* (2013.01)

(58) Field of Classification Search
CPC . A61F 2/01; A61F 2/011; A61F 2/013; A61B 17/221; A61B 2017/2212; A61B 2017/2215; A61B 2017/2217
See application file for complete search history.

(56) References Cited

U.S. PATENT DOCUMENTS 5,928,260 A * 7/1999 Chin ................. A61B 17/12022
                                                        604/107
6,042,598 A * 3/2000 Tsugita .................... A61F 2/01
                                                        606/200

(Continued)

FOREIGN PATENT DOCUMENTS

JP    2003-220062 A    8/2003
JP    2003-265487 A    9/2003

(Continued)

OTHER PUBLICATIONS

International Search Report (PCT/ISA/210) dated Sep. 6, 2016, by the Japanese Patent Office as the International Searching Authority for International Application No. PCT/JP2016/067622.

(Continued)

*Primary Examiner* — Dianne Dornbusch
(74) *Attorney, Agent, or Firm* — Buchanan Ingersoll & Rooney PC

(57) ABSTRACT

A medical device and a treatment method are disclosed that can be applied to body lumina with a wide range of inside diameters and can enhance a property for suction of a substance from the inside of a body lumen by restricting flow within the body lumen. The medical device includes an elongated shaft section; an expanding section that is an elastically deformable tubular body provided with a plurality of openings; a flexibly deformable tubular cover section that is coupled to an end portion on a proximal side of the expanding section, surrounds an outer periphery of the expanding section on the proximal side, but does not surround, and externally exposes, an outer periphery of the expanding section on a distal side; and a sheath capable of accommodating the expanding section and the cover section in a diameter-reduced state.

20 Claims, 16 Drawing Sheets

(56) References Cited

U.S. PATENT DOCUMENTS

| | | | | |
|---|---|---|---|---|
| 6,221,006 | B1* | 4/2001 | Dubrul | A61B 17/221 600/159 |
| 6,258,115 | B1* | 7/2001 | Dubrul | A61B 17/12109 606/191 |
| 6,336,934 | B1* | 1/2002 | Gilson | A61F 2/013 606/200 |
| 6,346,116 | B1* | 2/2002 | Brooks | A61F 2/01 606/159 |
| 6,575,996 | B1* | 6/2003 | Denison | A61F 2/013 606/200 |
| 6,638,293 | B1* | 10/2003 | Makower | A61B 1/3137 606/200 |
| 6,652,548 | B2* | 11/2003 | Evans | A61B 17/221 606/159 |
| 6,660,021 | B1* | 12/2003 | Palmer | A61B 17/221 606/200 |
| 6,695,813 | B1* | 2/2004 | Boyle | A61F 2/01 604/106 |
| 7,044,958 | B2* | 5/2006 | Douk | A61F 2/013 606/200 |
| 7,128,073 | B1* | 10/2006 | van der Burg | A61B 17/0057 128/887 |
| 7,172,614 | B2* | 2/2007 | Boyle | A61F 2/013 606/200 |
| 7,331,973 | B2* | 2/2008 | Gesswein | A61F 2/013 606/200 |
| 7,481,823 | B2* | 1/2009 | Broome | A61F 2/011 606/200 |
| 7,766,934 | B2* | 8/2010 | Pal | A61F 2/013 606/200 |
| 7,771,452 | B2* | 8/2010 | Pal | A61F 2/013 606/200 |
| 7,780,696 | B2* | 8/2010 | Daniel | A61B 17/221 606/200 |
| 7,862,577 | B2* | 1/2011 | Gray | A61F 2/01 606/200 |
| 8,109,962 | B2* | 2/2012 | Pal | A61F 2/013 606/200 |
| 8,182,507 | B2 | 5/2012 | Anderson et al. | |
| 8,262,689 | B2* | 9/2012 | Schneiderman | A61F 2/01 606/200 |
| 8,377,092 | B2* | 2/2013 | Magnuson | A61F 2/013 606/200 |
| 9,204,887 | B2* | 12/2015 | Cully | A61B 17/320725 |
| 9,445,829 | B2* | 9/2016 | Brady | A61B 17/320725 |
| 2002/0004667 | A1* | 1/2002 | Adams | A61F 2/013 606/200 |
| 2002/0091409 | A1 | 7/2002 | Sutton et al. | |
| 2002/0138094 | A1* | 9/2002 | Borillo | A61F 2/013 606/200 |
| 2003/0004536 | A1* | 1/2003 | Boylan | A61F 2/01 606/200 |
| 2004/0167568 | A1 | 8/2004 | Boyle et al. | |
| 2006/0041271 | A1 | 2/2006 | Bosma et al. | |
| 2009/0105644 | A1* | 4/2009 | Leonard | A61M 25/0662 604/104 |
| 2009/0198269 | A1* | 8/2009 | Hannes | A61B 17/221 606/200 |
| 2010/0268264 | A1* | 10/2010 | Bonnette | A61F 2/013 606/200 |
| 2016/0015402 | A1* | 1/2016 | Brady | A61L 31/022 606/159 |

FOREIGN PATENT DOCUMENTS

| | | |
|---|---|---|
| JP | 2007-125409 A | 5/2007 |
| JP | 2007-252895 A | 10/2007 |

OTHER PUBLICATIONS

Written Opinion (PCT/ISA/237) dated Sep. 6, 2016, by the Japanese Patent Office as the International Searching Authority for International Application No. PCT/JP2016/067622.

English language translation of the Written Opinion of the International Searching Authority and the International Search Report (Forms PCT/ISA/237 and PCT/ISA/210) dated Sep. 6, 2016, by the Japan Patent Office in corresponding International Application No. PCT/JP2016/067622. (6 pages).

* cited by examiner

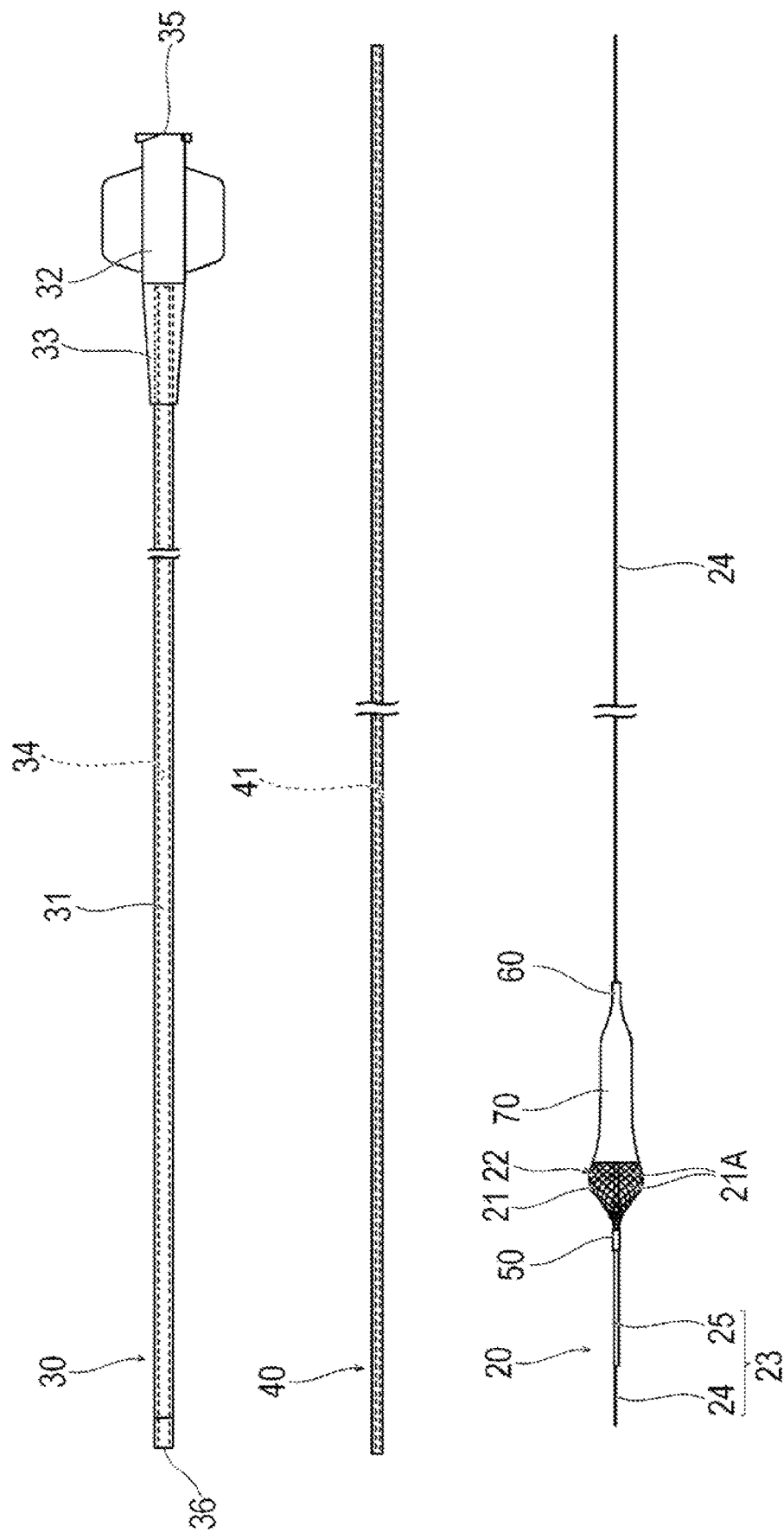

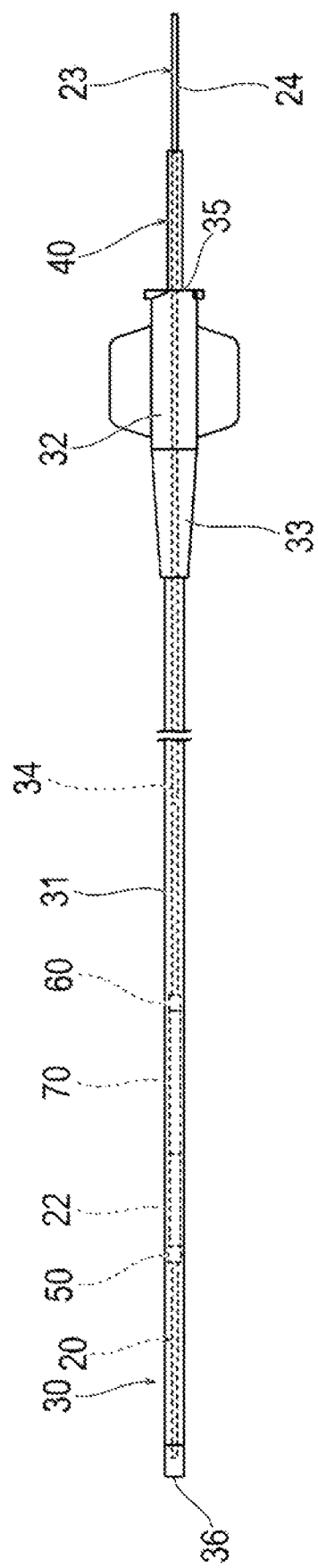

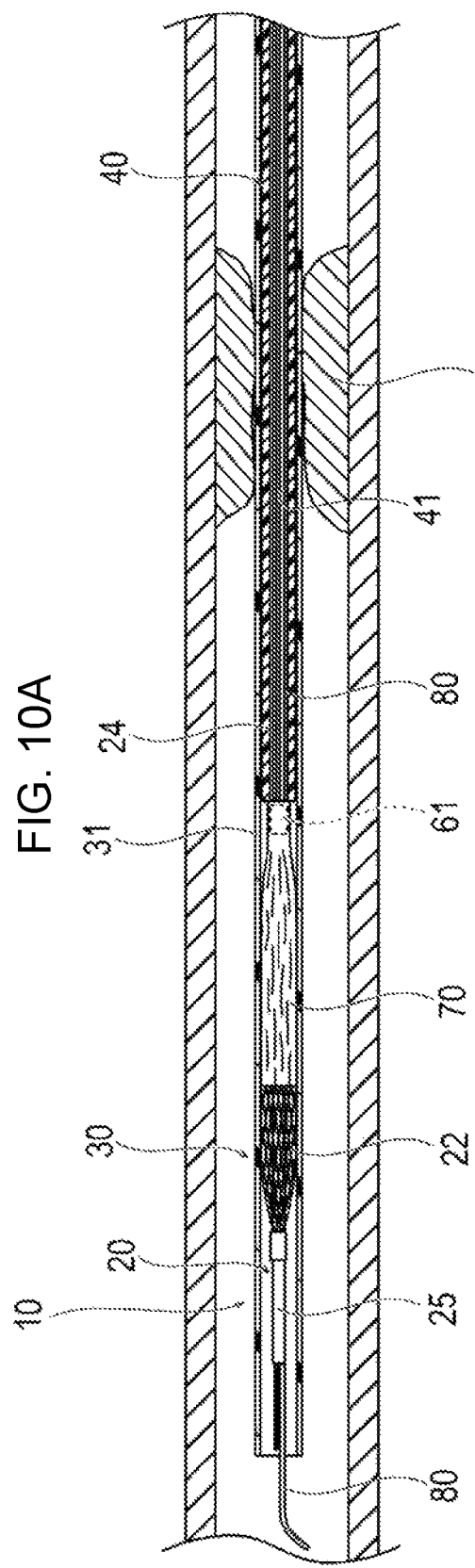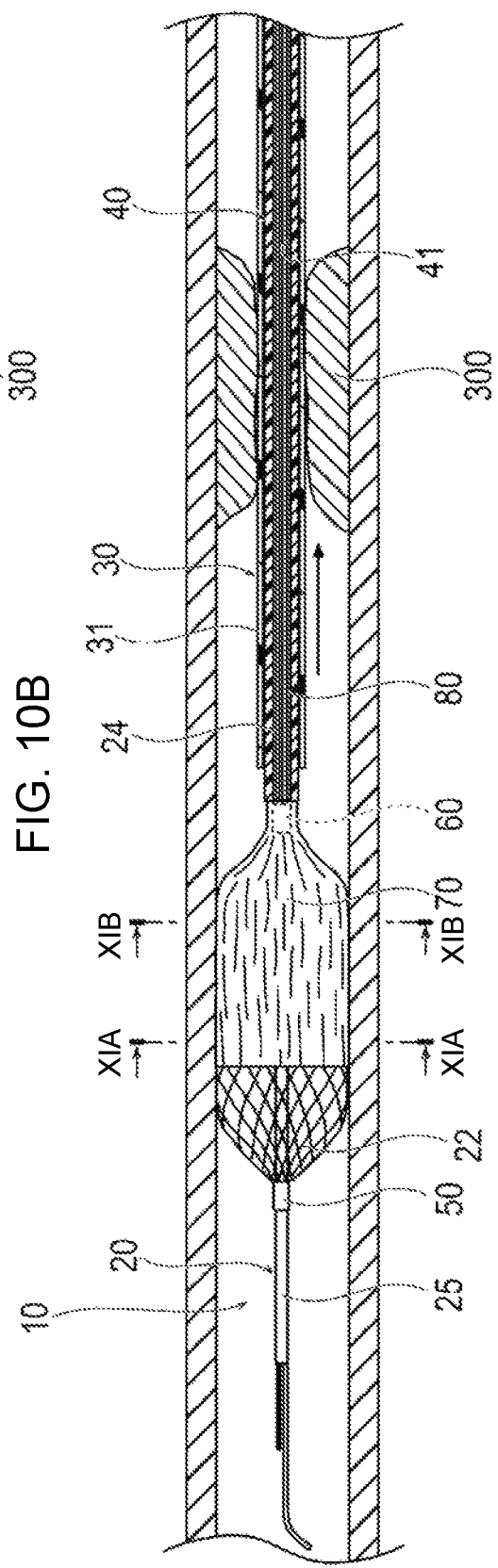

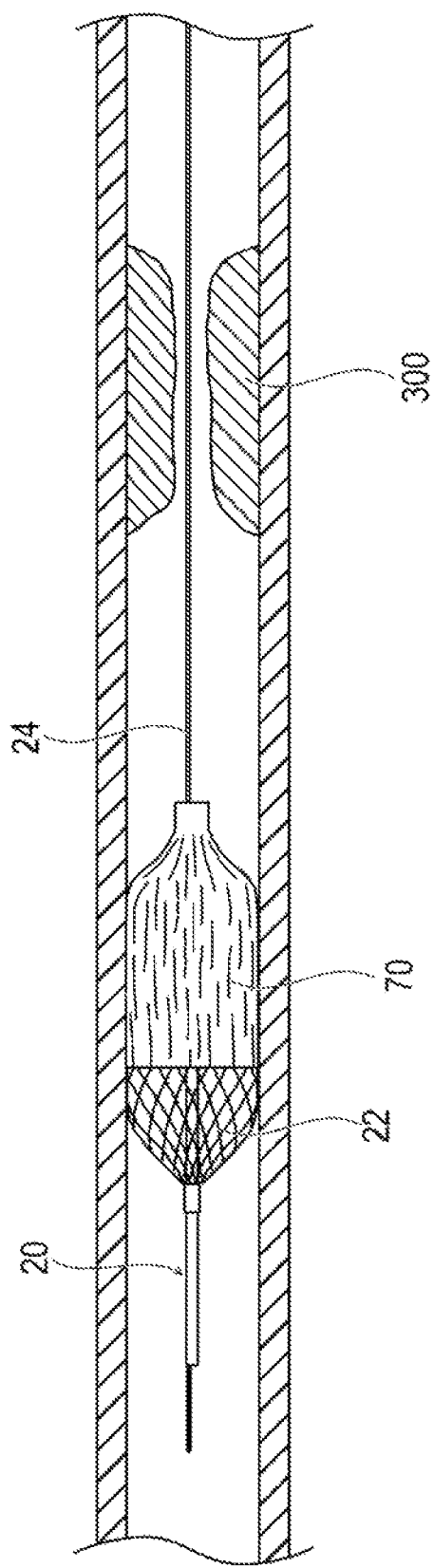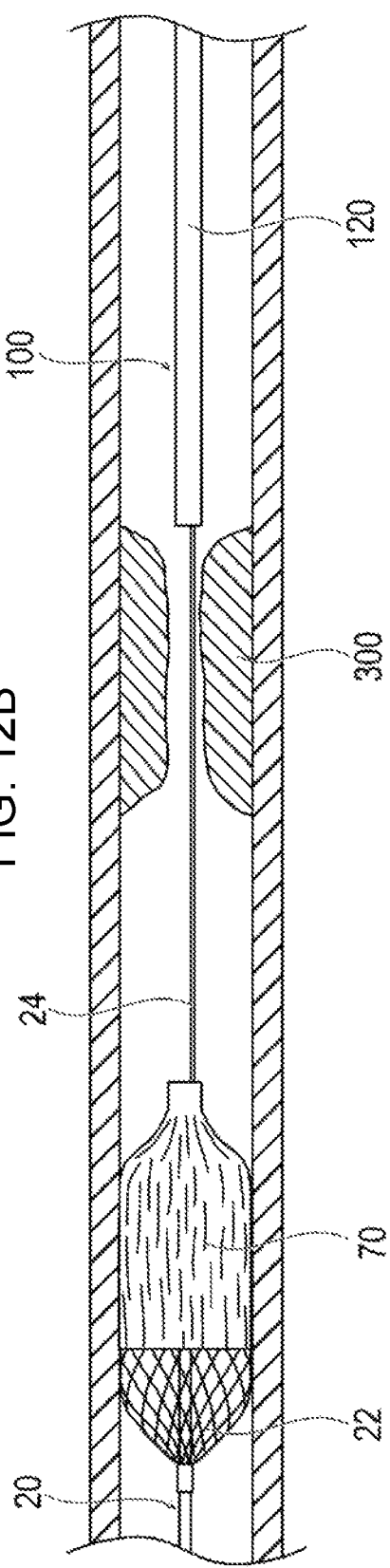

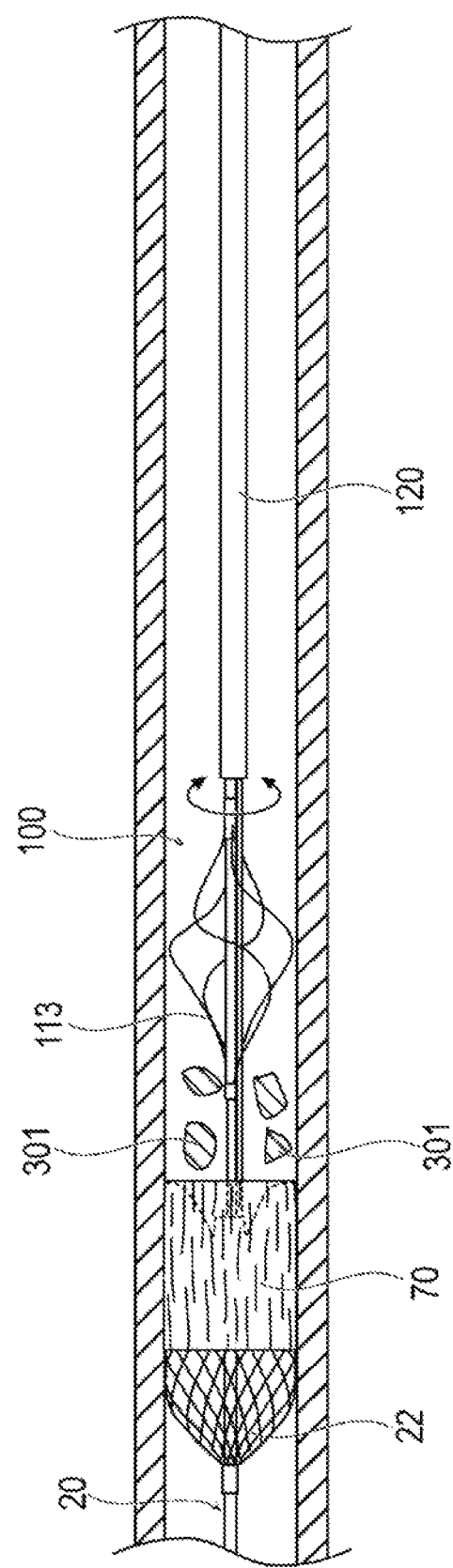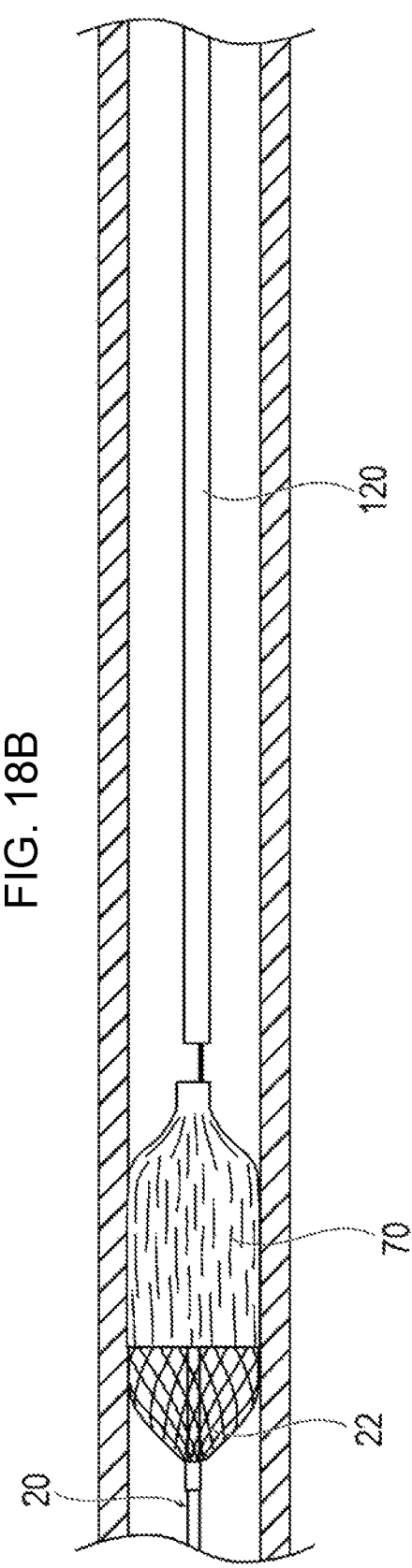

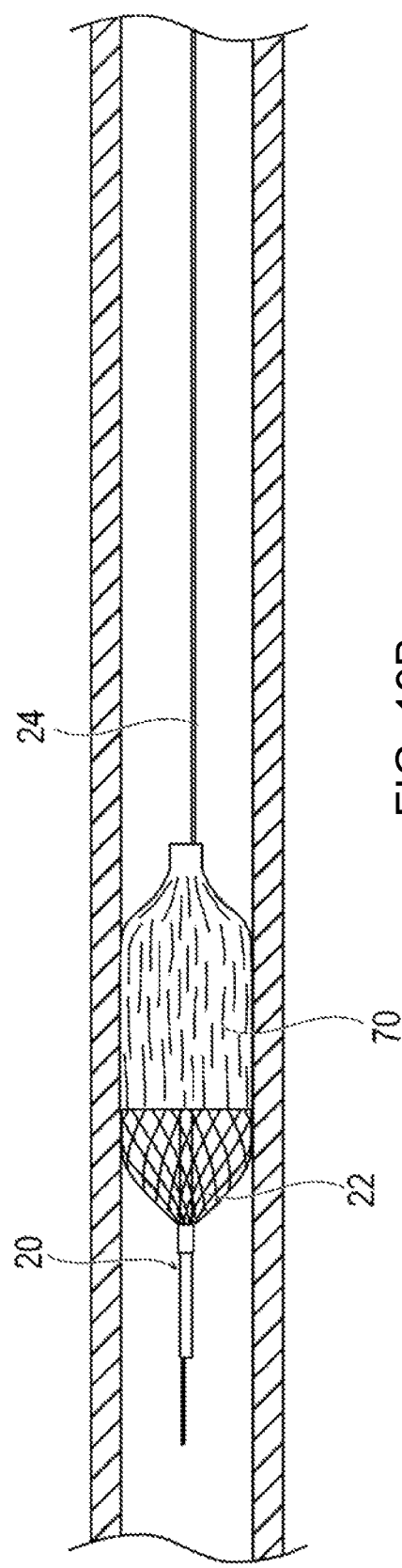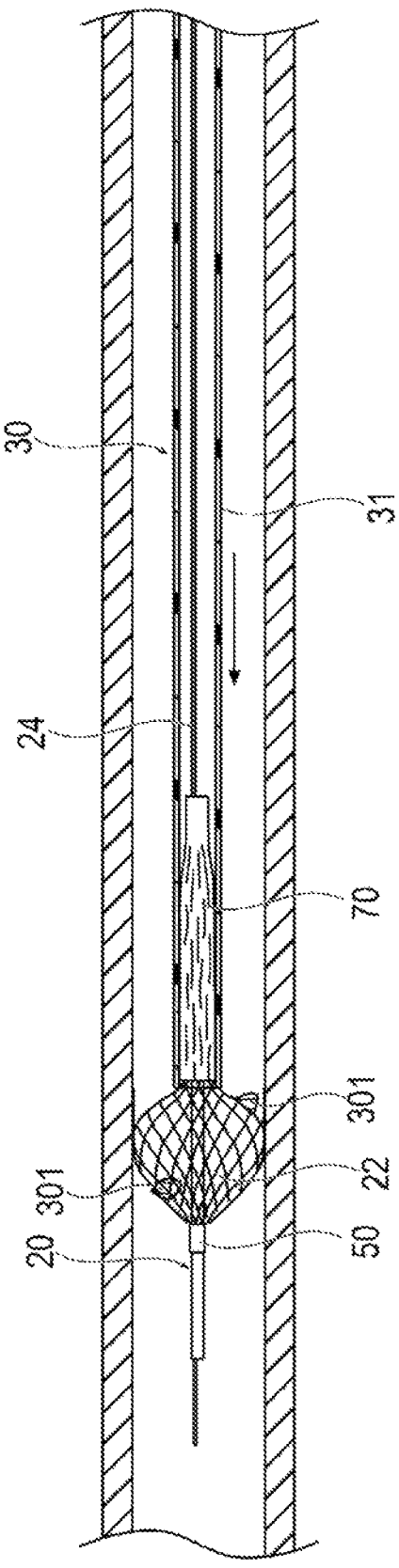

MEDICAL DEVICE AND TREATMENT METHOD

CROSS-REFERENCES TO RELATED APPLICATIONS

This application is a continuation of International Application No. PCT/JP2016/067622 filed on Jun. 14, 2016, which claims priority to Japanese Application No. JP2015-120973 filed on Jun. 16, 2015, the entire content of which are incorporated herein by reference.

TECHNICAL FIELD

The present disclosure relates to a medical device and a treatment method to be used for removing an object present in a body lumen.

BACKGROUND DISCUSSION

A thrombus formed in a portion of a vein, for example, may cause pain or swelling, and this may be treated by removing the thrombus with a thrombus-removing device that is percutaneously inserted into the vein. In such a treatment, if the entirety or a portion of the thrombus that has been separated from the wall of the blood vessel is carried by blood flow and reaches the lungs, there is a risk that pulmonary embolism will occur. Therefore, when such a treatment is performed, a thrombolytic agent is used before, during, and/or after the treatment, or the separated thrombus is removed as thoroughly as possible by suction during the treatment. However, even when these processes are carried out, there is still a possibility that a separated thrombus that is dangerously large from a clinical point of view will reach, for example, the lungs.

As a method for avoiding the pulmonary embolism, there has been known, for example, an IVC filter (Inferior Vena Cava filter) for collecting thrombi that flow through a blood vessel (see, for example, U.S. Pat. No. 8,182,507).

However, since the openings in the IVC filter is relatively large, only large thrombi can be collected by the filter. In addition, the IVC filter is designed for the inferior vena cava, and is not suited to blood vessels thinner than the inferior vena cava. In addition, it is extremely difficult to suck the collected thrombi, since the thrombi need to be sucked against strong blood flow.

SUMMARY

In accordance with an exemplary embodiment, a medical device and a treatment method are disclosed which can be applied to body lumina with a wide range of inside diameters and can enhance a property for suction of a substance from within a body lumen by restricting flow within the body lumen.

In accordance with an exemplary embodiment, a medical device is disclosed, which is configured to be inserted into a body lumen for restricting flow within the body lumen, the medical device including: an elongated shaft section; an expanding section that is an elastically deformable tubular body including a plurality of openings, the expanding section including a central portion greater in outside diameter than end portions on both sides of the tubular body in a natural state in which no external force is applied, with the shaft section being coupled to at least one of the end portions; a flexibly deformable tubular cover section that is coupled to an end portion on a proximal side of the expanding section, surrounds an outer periphery of the expanding section on the proximal side, but does not surround, and externally exposes, an outer periphery of the expanding section on a distal side; and a sheath capable of accommodating the expanding section and the cover section in a diameter-reduced state.

In the medical device configured as above, with the expanding section and the cover section released out of the sheath, the expanding section expands by its own elastic force in conformity with the shape of the body lumen, whereby the cover section is pressed against the body lumen by the expanding section, and that portion of the expanding section which is not surrounded by the cover section makes direct contact with the body lumen and is fixed. Therefore, owing to the expanding section which expands by its own elastic force, the medical device is applicable to body lumina with a wide range of inside diameters, the flow within a body lumen can be effectively restricted by the cover section, and a property for suction of a substance from the inside of the body lumen can be enhanced.

A medical device is disclosed configured to be inserted into a body lumen for restricting flow within the body lumen, the medical device comprising: an elongated shaft section; an expanding section that is an elastically deformable tubular body including a plurality of openings and is coupled to the elongated shaft section; and a flexibly deformable tubular cover section that is coupled to an end portion on a proximal side of the expanding section, and wherein the flexibly deformable tubular cover surrounds the proximal side of the expanding section and exposes a distal side of the expanding section.

A treatment method is disclosed for removing an object generated at a lesion part in a body lumen by suction by use of a medical device, the medical device having an elongated shaft section, an expanding section that is an elastically deformable tubular body including a plurality of openings and is coupled to the elongated shaft section, and a flexibly deformable tubular cover section that is coupled to an end portion on a proximal side of the expanding section, and wherein the flexibly deformable tubular cover surrounds the proximal side of the expanding section and exposes a distal side of the expanding section, the treatment method comprising: pushing out the expanding section from the sheath to a downstream side of the lesion part in the body lumen, with the side of the expanding section being surrounded by the cover section on the upstream side, to allow the expanding section to expand by its own elastic force to press the cover section against the body lumen, and to cause an expanding section's part not surrounded by the cover section to make direct contact with the body lumen and be fixed to the body lumen; breaking the object generated at the lesion part in the body lumen into fragments; and inserting into the body lumen a device provided with a suction port and capable of sucking, and sucking the fragments of the object.

BRIEF DESCRIPTION OF THE DRAWINGS

FIG. 1 is a plan view of a medical device according to an exemplary embodiment.

FIG. 2 is a plan view depicting a combined state of a restrictor, a pressing shaft, and a sheath of the medical device according to the exemplary embodiment.

FIG. 3A depicts an expanded state of the expanding section, and FIG. 3B depicts a contracted state of the expanding section.

FIGS. 10A and 10B depict sectional views depicting a state inside a blood vessel, where FIG. 10A depicts a state when the medical device is inserted in the blood vessel, and FIG. 10B depicts a state in which the expanding section and a cover section are expanded inside the blood vessel.

FIGS. 12A and 12B depict sectional views depicting a state inside a blood vessel, where FIG. 12A depicts a state when the restrictor is left indwelling in the blood vessel, and FIG. 12B depicts a state when the removing device is inserted in the blood vessel.

FIG. 13A depicts a state when a stirring unit of the removing device is expanded, and FIG. 13B depicts a state when a thrombus is broken by the stirring unit into fragments.

FIGS. 18A and 18B depict sectional views depicting a state inside a blood vessel, where FIG. 18A depicts a state when the thrombus adhering to the restrictor is sucked, and FIG. 18B depicts a state when the stirring unit is accommodated in an outermost sheath body.

FIGS. 19A and 19B depict sectional views depicting a state inside a blood vessel, where FIG. 19A depicts a state when the removing device has been withdrawn from the inside of the blood vessel, and FIG. 19B depicts a state when a cover section is accommodated in a sheath.

DETAILED DESCRIPTION

Figure 3A:
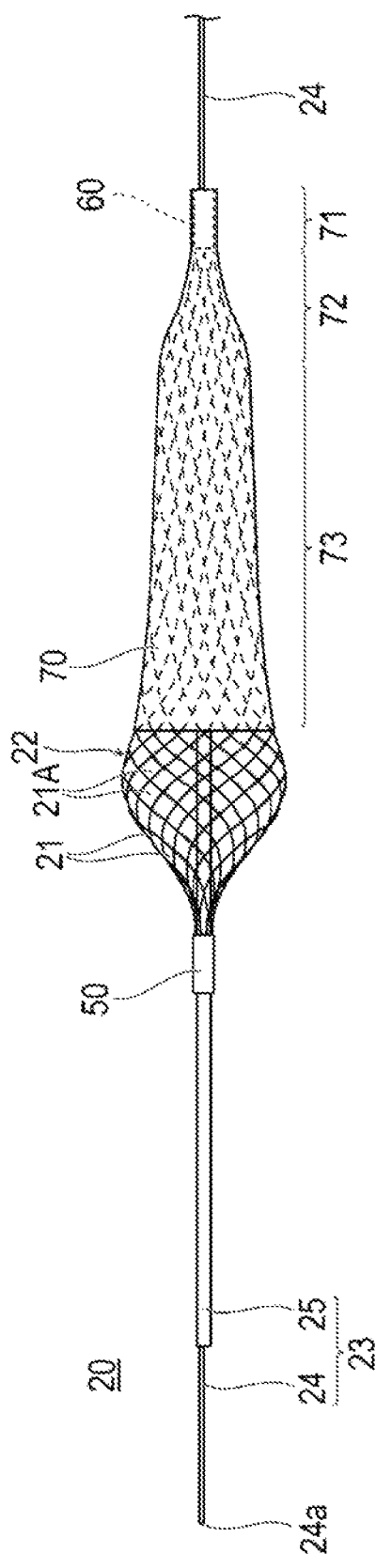
FIGS. 3A and 3B depict plan views depicting an expanding section of the restrictor, where

An embodiment of the present disclosure will be described below, referring to the drawings. Note that dimensional ratios in the drawings may be exaggerated, for convenience of explanation, and be different from the actual ratios.

A medical device 10 according to an exemplary embodiment of the present disclosure is used to restrain flow in a blood vessel, for removing by suction an object such as a thrombus or a plaque present in the blood vessel. Note that herein the side of insertion of the device into the blood vessel is referred to as the "distal side," and the side of the operator's hand is referred to as the "proximal side." In addition, the object to be removed is not necessarily limited to a thrombus or a plaque, and any object that can be present in a body lumen is applicable.

As depicted in FIGS. 1 and 2, the medical device 10 according to the embodiment of the present disclosure includes a restrictor 20 for restricting flow of blood in a blood vessel, a sheath 30 capable of accommodating the restrictor 20, and a pressing shaft 40 used to push the restrictor 20 out of the sheath 30.

The restrictor 20 includes an expanding section 22 which is an elastically deformable mesh-formed tubular body provided with a plurality of openings 21A, a cover section 70 partly surrounding an outer periphery of the expanding section 22, and an elongated shaft section 23 penetrating the expanding section 22 and the cover section 70.

As depicted in FIGS. 1 to 6, the shaft section 23 includes an elongated wire portion 24, and a guidewire tubular body 25 which is fixed to either an inner peripheral surface 57 of an inner tube 54 provided at a distal portion of the expanding section 22 or an inner peripheral surface 67 of an inner tube 64 provided at a proximal portion of the expanding section 22 (in this embodiment, the inner peripheral surface 67) and which is formed therein with a guidewire lumen 26. The guidewire tubular body 25 is formed with a wire through-hole 27 in which the wire portion 24 is inserted and fixed, in parallel to the guidewire lumen 26. In addition, a tip 24a of the wire portion 24 may be fixed to the inner peripheral surface 67 of the inner tube 64 at the proximal portion of the expanding section 22. In this instance, the wire portion 24 and the guidewire tubular body 25 of the shaft section 23 are separate members. The shaft section 23 has the guidewire tubular body 25, and is fixed to the inner peripheral surface 57 of the inner tube 54 at the distal portion of the expanding section 22 or the inner surface 67 of the inner tube 64 at the proximal portion of the expanding section 22.

The material constituting the wire portion 24 constituting the shaft section 23 is not specifically restricted, and, for example, stainless steel and shape memory alloys can be used suitably. The material constituting the guidewire tubular body 25 constituting the shaft section 23 is not particularly limited, and, for example, plastic materials such as polyimides, polyamides, etc., and stainless steel, and shape memory alloys can be used suitably.

Figure 3B:
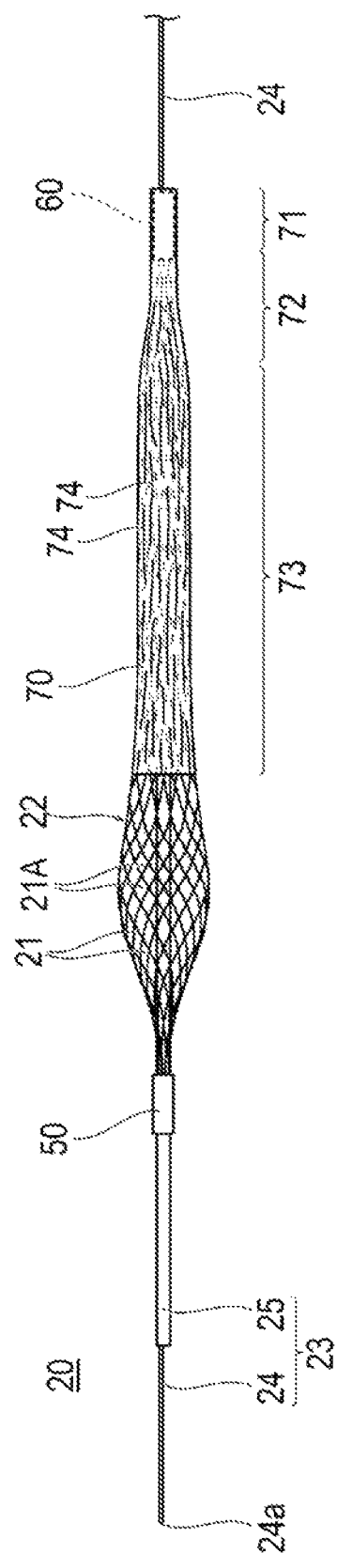

As depicted in FIGS. 3A and 3B, the expanding section 22 includes a plurality of flexibly deformable wires 21 knitted in a mesh form, and a distal-side connection portion 50 and a proximal-side connection portion 60 which are connected to the guidewire tubular body 25 of the shaft section 23. In accordance with an exemplary embodiment, an outer peripheral surface of the guidewire tubular body 25 of the shaft section 23 is fixed at either one of the inner peripheral surfaces 57 and 67 of the inner tubes 54 and 64 at the distal-side connection portion 50 or the proximal-side connection portion 60. At the other of the inner peripheral surfaces 57 and 67, the inner peripheral surface 54 and 64 and the outer peripheral surface of the guidewire tubular body 25 are not fixed but are disposed slidably. The expanding section 22 is formed in a tubular shape by knitting the plurality of wires 21 so that the openings 21A are provided between the wires 21.

The expanding section 22 can be deformed into an expanded state in which a diameter of the expanding section 22 is enlarged by elastic forces (restoring forces) of the wires 21 themselves in a state in which no external force is applied, as depicted in FIG. 3A, and a contracted state in which its outside diameter is reduced through its elastic deformation, as depicted in FIG. 3B.

Figure 5:
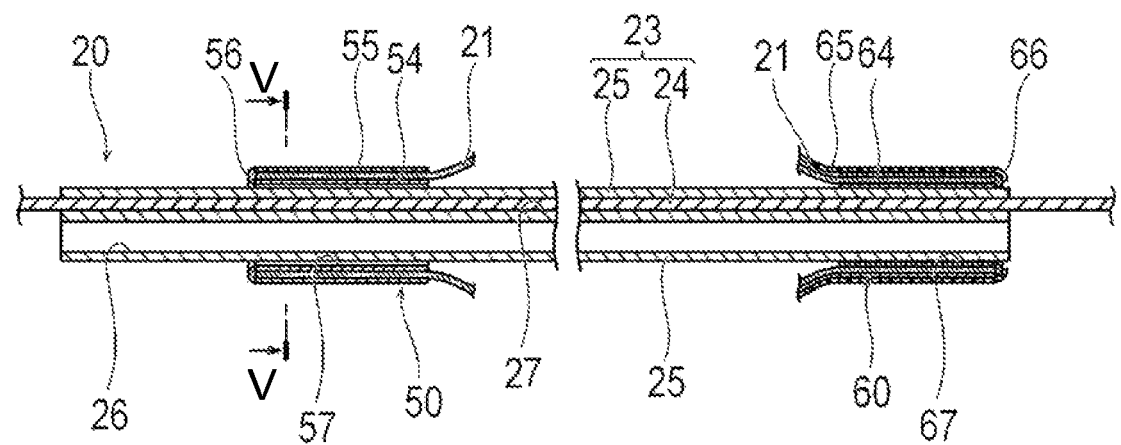
FIG. 5 is an enlarged sectional view of a proximal-side connection portion and a distal-side connection portion.
Figure 6:
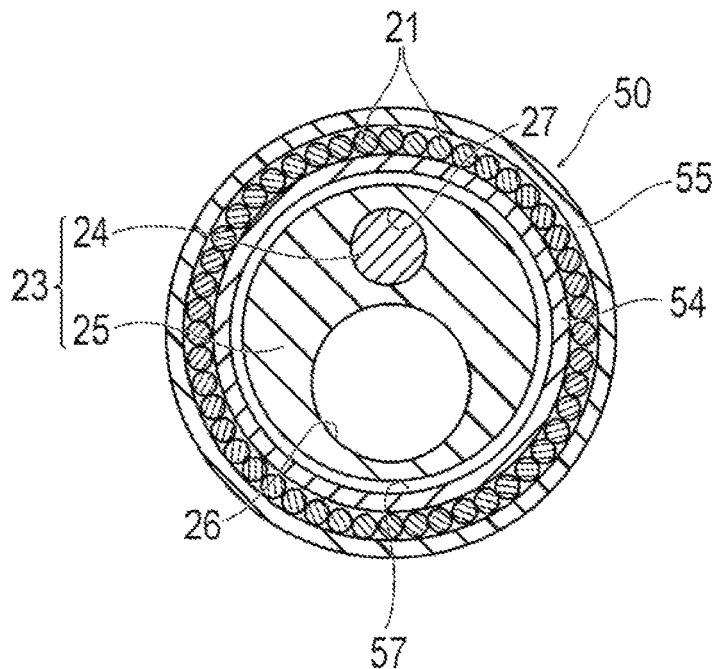
FIG. 6 is a sectional view taken along line V-V of FIG. 5.

As depicted in FIGS. 3A, 3B, and 5, the proximal-side connection portion 60 includes the inner tube 64 located on the inside of the wires 21, an outer tube 65 located on the outside of the wires 21, and a joint portion 66 by which the inner tube 64 and the outer tube 65 are joined to each other at an end portion thereof, with the wires 21 being sandwiched and fixed between the inner tube 64 and the outer tube 65. At the proximal-side connection portion 60, the inner tube 64 is secured to the guidewire tubular body 25. Note that the joint portion 66 may not necessarily be provided, so long as the wires 21 can be fixed.

As depicted in FIGS. 3A to 6, the distal-side connection portion 50 includes the inner tube 54 located on the inside of the wires 21, an outer tube 55 located on the outside of the wires 21, and a joint portion 56 by which the inner tube 54 and the outer tube 55 are joined to each other at an end portion thereof, with the wires 21 being sandwiched and fixed between the inner tube 54 and the outer tube 55. The distal-side connection portion 50 is movable in the axial direction relative to the guidewire tubular body 25, with the guidewire tubular body 25 being slidably inserted inside the inner tube 54. Note that the connection portion 56 may not necessarily be provided, so long as the wires 21 can be fixed.

In accordance with an exemplary embodiment, the distal-side connection portion 50 is slid toward the proximal side relative to the guidewire tubular body 25 to approach the proximal-side connection portion 60 (see FIG. 3A) when the expanding section 22 comes into an expanded state, and the distal-side connection portion 50 is slid toward the distal side relative to the guidewire tubular body 25 to come away from the proximal-side connection portion 60 (see FIG. 3B) when the expanding section 22 comes into a contracted state. With the distal-side connection portion 50 capable of coming toward or away from the proximal-side connection portion 60, the outside diameter of the knitted expanding section 22 can be varied largely.

The number of the wires 21 is not particularly limited, and is, for example, 4 to 72. In addition, the conditions of knitting of the wires 21 are not specifically restricted.

The outside diameter of the wires 21 can be appropriately selected according to the material of the wires 21 and the use of the expanding section 22, and can be, for example, 20 μm to 300 μm.

The material constituting the wires 21 is preferably a flexible material; for example, shape memory alloys to which a shape memory effect and/or superelasticity is imparted by a heat treatment, stainless steel, Ta, Ti, Pt, Au, W, polyolefins such as polyethylene, polypropylene, polyamides, polyesters such as polyethylene terephthalate, fluoro-polymers such as ETFE, PEEK (polyether-ether ketone), and polyimides can be used suitably. In accordance with an exemplary embodiment, as the shape memory alloy, those based on Ni—Ti, Cu—Al—Ni, or Cu—Zn—Al and combinations thereof can be used preferably. Examples of a structure obtained by combining a plurality of materials include a structure obtained by coating a Pt core wire with a Ni—Ti alloy, and a structure obtained by plating a Ni—Ti core wire with gold, for imparting radiopacity.

The outside diameter of the outer tubes 55 and 65 is not particularly limited, and can be, for example, 0.3 mm to 3.0 mm. The inside diameter of the inner tubes 54 and 64 is not specifically restricted, and can be for example, 0.1 mm to 2.0 mm.

The material or materials constituting the inner tubes 54 and 64 and the outer tubes 55 and 65 are not specifically restricted; for example, stainless steel and shape memory alloys can be used suitably.

In accordance with an exemplary embodiment, the outside diameter of the expanding section 22 in its expanded state can be appropriately selected according to the inside diameter of a blood vessel to which the medical device 10 is applied, and the outside diameter of the expanding section 22 can be, for example, 1 mm to 20 mm. The outside diameter of the expanding section 22 in its contracted state can be appropriately selected according to the inside diameter of the blood vessel to which the medical device 10 is applied, and the outside diameter of the expanding section 22 can be, for example, 0.3 mm to 4.0 mm. The length in the axial direction of the expanding section 22 in its contracted state can be appropriately selected according to the blood vessel to which the medical device 10 is applied, and the outside diameter of the expanding section 22 can be, for example, 20 mm to 150 mm.

As depicted in FIGS. 3A and 3B, the cover section 70 is a member formed in a tubular shape from a thin film in such a manner as to cover the outer periphery on the proximal side of the expanding section 22. The cover section 70 may have or may not have a liquid flowing property. In the case where the cover section 70 has a fluid flowing property, the cover section 70 can be formed with a plurality of holes, and, in this case, the size of the holes is smaller than the openings 21A formed in the expanding section 22. In accordance with an exemplary embodiment, the cover section 70 plays the role of restricting blood flow in such a manner that a thrombus in a blood vessel can be effectively removed by suction by a removing device 100 which will be described later. Therefore, the size of the holes, in the case where the cover section 70 is provided with the holes in the blood vessel, is preferably such a size as to be able to restrict blood flow to such an extent that a thrombus can be sucked by the removing device 100. The diameter of the holes can be, for example, not greater than 1 mm.

The cover section 70 includes a cover proximal portion 71 secured to an outer peripheral surface of the proximal-side connection portion 60, a cover taper portion 72 of which the inside and outside diameters increase in a taper form toward the distal side from the cover proximal portion 71, and a cover distal portion 73 of which the inside and outside diameters slightly increase, though not so largely as the cover taper portion 72, toward the distal side from the cover taper portion 72. The cover section 70 does not cover a distal portion of the expanding section 22. The cover distal portion 73 is slightly increased in inside and outside diameters toward the distal side, due to an influence of an expanding force of the expanding section 22 not covered by the cover section 70. The cover section 70 is secured to the proximal-side connection portion 60 only at the cover proximal portion 71; the cover taper portion 72 and the cover distal portion 73 are not secured to the expanding section 22 but only covers the expanding section 22. For this reason, the intersection angle of the wires 21 constituting the expanding section 22 can vary without being hindered by the cover section 70, so that the expanding section 22 is flexibly deformable. In addition, since the outside diameter of the expanding section 22 varies attended by variation in the intersection angle of the wires 21, the expanding section 22 decreases in its length in the axial direction when it is enlarged in diameter, whereas the cover section 70 is formed from a high-strength material so as not to be broken notwithstanding that cover section 70 is relatively thin. Therefore, the cover section 70 is formed with folded-back portions 74 overlapping, or with its outside diameter varied when the folded-back portions 74 are stretched, and the variation in its length in the axial direction is smaller than that of the expanding section 22. Accordingly, the position where the expanding section 22 and the cover section 70 make contact with each other when expanded is different from that when contracted. For example, at the time of transition from an expanded state into a contracted state, a distal-side end portion of the cover section 70 is moved proximally relative to the expanding section 22 (see FIG. 3B), and, conversely, at the time of transition from the contracted state into the expanded state, the distal-side end portion of the cover section 70 is moved distally relative to the expanding section 22 (see FIG. 3B). Thus, the mutual contact position of the expanding section 22 and the cover section 70 in their expanded state is different from that in their contracted state. Since the expanding section 22 and the cover section 70 are coupled together only at the proximal-side end portion, however, the difference in the contacting position can be absorbed.

The maximum outside diameter of the cover section 70 is smaller than the maximum outside diameter of an exposed portion of the expanding section 22 that is not covered by the cover section 70. In other words, by covering the proximal side of the expanding section 22, the cover section 70 forcibly helps prevent a proximal-side portion of the expanding section 22 from being enlarged in diameter. Since a proximal portion of the expanding section 22 is covered by the cover section 70, a maximum-outside-diameter portion of the expanding section 22 is located on the distal side as compared to a central portion of the expanding section 22.

As depicted in FIG. 3B, the cover section 70 is reduced in diameter in such a manner as to generate the folded-back portions 74 folded back so as to overlap when the cover section 70 is contracted, and edge portions of the folded-back portions 74 formed in wrinkle form extend in the axial direction. In accordance with an exemplary embodiment, It can be preferable that a plurality of the folded-back portions 74 are formed in the circumferential direction, and, in addition, they are not formed over the whole length in the axial direction of the cover section 70 but are formed intermittently to be shorter than the whole length in the axial direction of the cover section 70, thereby being formed in plurality in the axial direction. Note that each of the folded-back portions 74 may be formed over the whole length in the axial direction of the cover section 70.

Figure 4:
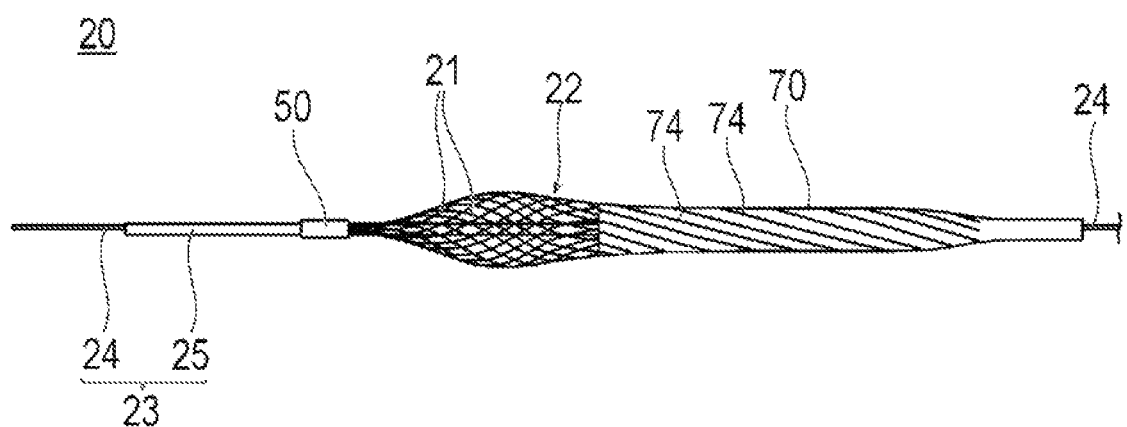
FIG. 4 is a plan view depicting a contracted state of the expanding section of the restrictor.

As depicted in FIG. 3A, when expanded, the cover section 70 is enlarged in diameter in such a manner that the folded-back portions 74 are stretched and that the number of overlapping portions decreases. Note that when the cover section 70 is expanded, the folded-back portions 74 may not be stretched completely and some overlapping portions may be left partially. In addition, as depicted in FIG. 4, before the cover section 70 is inserted into the sheath 30, the folded-back portions 74 may be inclined at an angle relative to the axial direction, and a plurality of the folded-back portions 74 oblique relative to the axial direction may be provided in the circumferential direction, which helps ensure that when the cover section 70 is inserted into the sheath 30 or is released out of the sheath 30, the cover section 70 can be relatively easily inserted and released while being twisted, and the resistance at the time of inserting and releasing the cover section 70 can be reduced. Note that the cover section 70 may be formed from a highly elastic material so that it can be enlarged and reduced in diameter, without generating the folded-back portions.

In accordance with an exemplary embodiment, frictional resistance between the cover section 70 and a blood vessel is smaller than that between the expanding section 22 and the blood vessel. Therefore, with the maximum-outside-diameter portion of the expanding section 22 set larger than the maximum-outside-diameter portion of the cover section 70, fixation to a blood vessel can be provided mainly by the expanding section 22 rather than the cover section 70, and the restrictor 20 can be effectively fixed to the blood vessel.

In accordance with an exemplary embodiment, if the outside diameter of the cover section 70 is too large, the accommodating space inside the sheath 30 becomes insufficient when the cover section 70 is accommodated in the sheath 30; as a result, the resistance at the time of accommodating the cover section 70 into the sheath 30 and the resistance at the time of releasing the cover section 70 out of the sheath 30 are enlarged. Accordingly, it can be preferable that the outside diameter of the cover section 70 is set to a minimum necessary value.

In addition, if the cover section 70 is too long in the axial direction, the accommodating space inside the sheath 30 becomes insufficient when the cover section 70 is accommodated in the sheath 30; as a result, the resistance at the time of accommodating the cover section 70 into the sheath 30 and the resistance at the time of releasing the cover section 70 out of the sheath 30 are enlarged. Therefore, it can be preferable that the length of the cover section 70 is set to a minimum necessary value.

The material constituting the cover section 70 is preferably a material which is thin, has such a strength as not to be broken even when deformed, and has a small friction resistance such as to be slidable within the sheath 30; as the material, for example, polyethylene and the like are applicable. The thickness of the cover section 70 is not particularly limited, and can be, for example, 5 µm to 30 µm. It is preferable that the cover section 70, in its length in the axial direction in an expanded state, covers 30% to 70% of the expanding section 22.

The cover section 70 may not necessarily be a film-shaped member; for example, it may be a mesh-formed film body or a knitted body obtained by knitting a wire.

As depicted in FIGS. 1 and 2, the sheath 30 includes a sheath tubular body 31, a hub 32, and an anti-kinking protector 33. The sheath tubular body 31 is provided with a lumen 34 in which the restrictor 20 can be accommodated, and the sheath tubular body 31 is open at a tubular body opening 36 formed at a distal-side end portion. The hub 32 is fixed to a proximal-side end portion of the sheath tubular body 31, and is provided with a hub opening 35, which communicates with the lumen 34. The anti-kinking protector 33 is a flexible member covering a coupling part of the sheath tubular body 31 and the hub 32, and restrains the sheath tubular body 31 from kinking.

The material constituting the sheath tubular body 31 is not specifically restricted, and, for example, polyolefins such as polyethylene, polypropylene, ethylene-propylene copolymer, ethylene-vinyl acetate copolymer, polyvinyl chloride, polystyrene, polyamides, polyimides, combinations thereof and the like can be used. The sheath tubular body 31 may be formed from a plurality of materials, and a reinforcing member such as wire may be embedded therein.

The pressing shaft 40 is a tubular body capable of being accommodated in the lumen 34 of the sheath 30, and is formed therein with a pushing-out lumen 41 in which the wire portion 24 of the restrictor 20 can be inserted. The inside diameter of the pushing-out lumen 41 is smaller than the outside diameter of the proximal-side connection portion 60 of the restrictor 20. Therefore, the proximal-side connection portion 60 cannot enter the pushing-out lumen 41, and, accordingly, the proximal-side connection portion 60 can be pushed distally by the pressing shaft 40.

Now, the removing device 100 for removing a thrombus by being inserted into a blood vessel will be described below.

Figure 7:
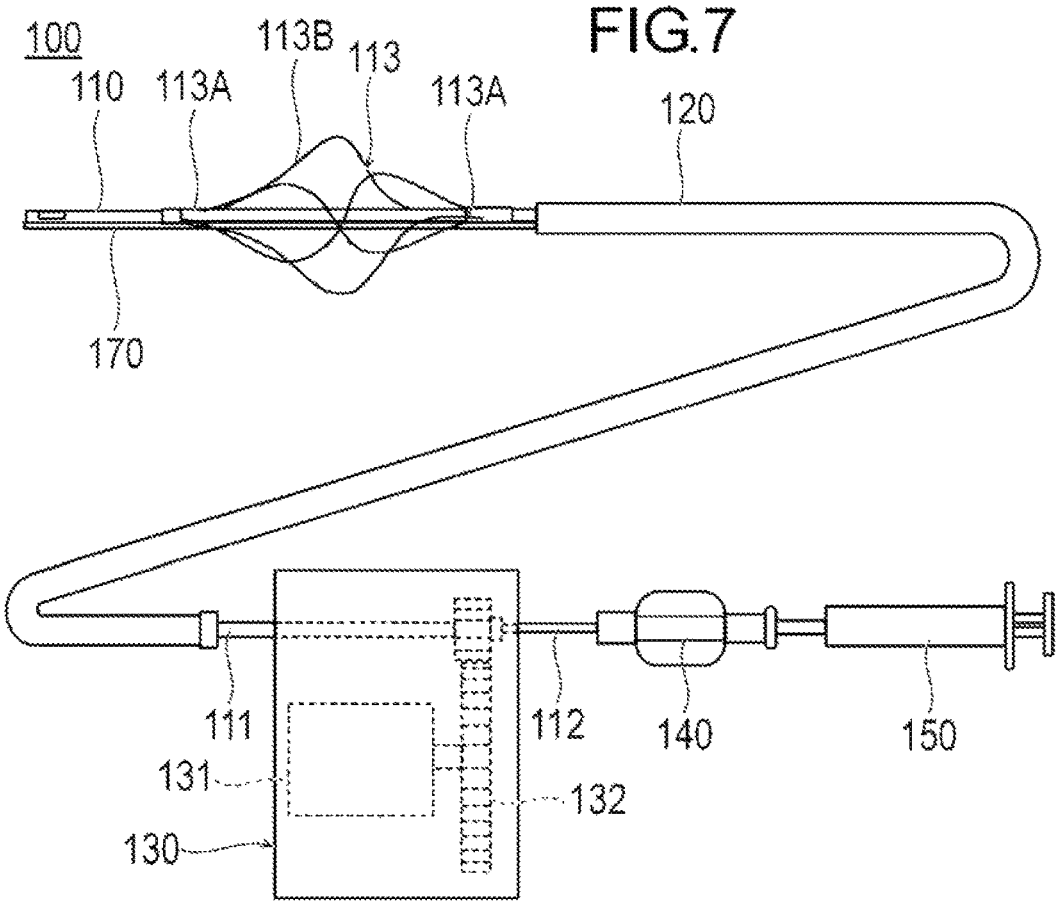
FIG. 7 is a plan view depicting a removing device.
Figure 8:
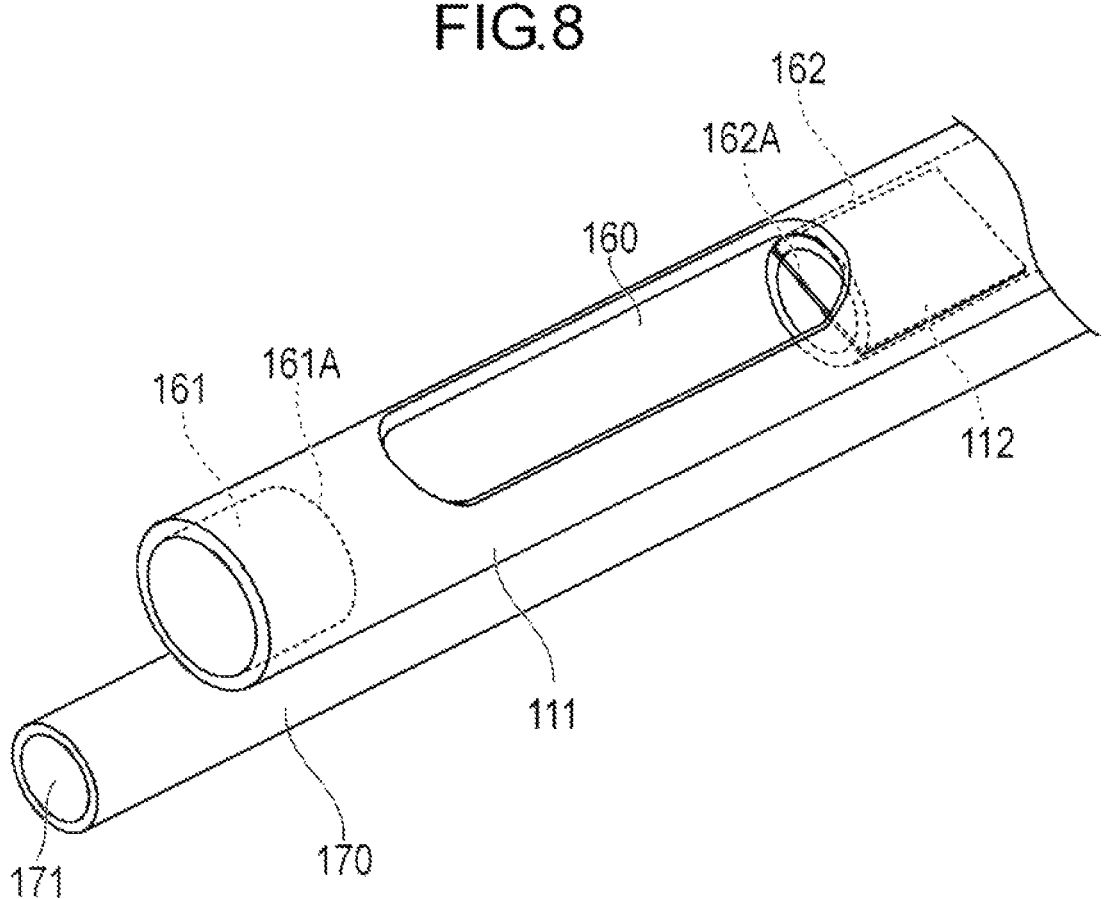
FIG. 8 is a perspective view depicting a distal portion of the removing device.
Figure 9:
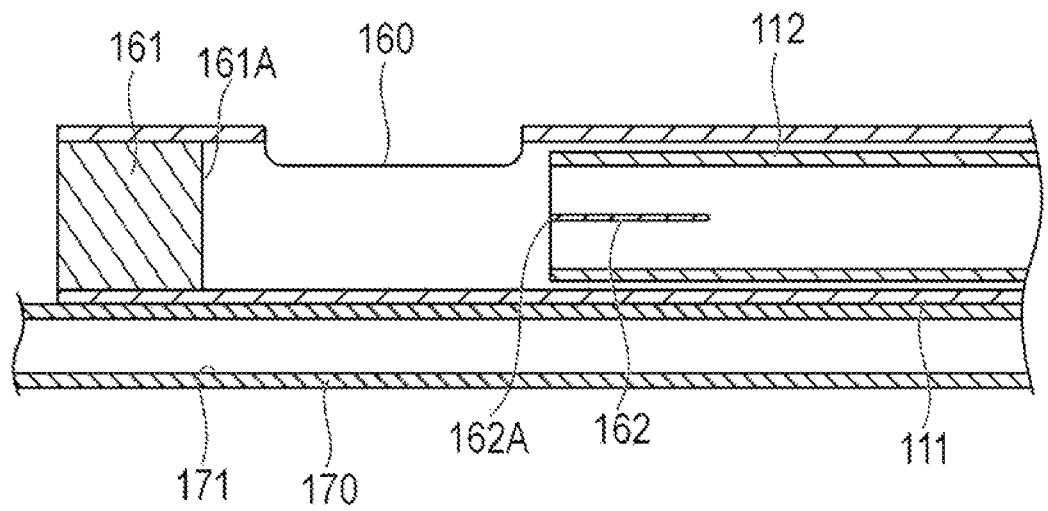
FIG. 9 is a sectional view depicting the distal portion of the removing device.

As depicted in FIGS. 7 to 9, the removing device 100 includes a shaft main body 110 formed in an elongated shape, an outermost sheath body 120 in which the shaft main body 110 is accommodated and which is slidable in the axial direction relative to the shaft main body 110, and a guidewire tubular body 170 formed with a second guidewire lumen 171. The removing device 100 further has a rotary drive unit 130 capable of rotating the shaft main body 110, a hub 140 provided at a proximal-side end portion of the shaft main body 110, and a syringe 150 connected to the proximal side of the hub 140.

The shaft main body 110 is composed of a shaft outer tube 111 and a shaft inner tube 112, which are each formed in an elongated hollow shape. The shaft outer tube 111 and the shaft inner tube 112 are each provided therein with a lumen. The inside diameter of the shaft outer tube 111 is greater than the outside diameter of the shaft inner tube 112, and the shaft inner tube 112 is accommodated in the hollow inside of the shaft outer tube 111. In addition, the shaft inner tube 112 is slidable in the axial direction relative to the shaft outer tube 111.

The shaft outer tube 111 has a distal-side end portion forming a distal portion of the shaft main body 110, and has a proximal-side end portion located at the rotary drive unit 130. The shaft inner tube 112 has a proximal-side end portion extending further proximally beyond a proximal-side end portion of the shaft outer tube 111, to be connected to the hub 140. In accordance with an exemplary embodiment, it is possible to suck the hollow inside of the shaft inner tube 112 by the syringe 150 connected to the hub 140, thereby to establish a negative-pressure state in the hollow inside.

The guidewire tubular body 170 is disposed along the shaft outer tube 111, being secured to the shaft outer tube 111. The guidewire tubular body 170 is formed with the second guidewire lumen 171 in which a guidewire can be inserted.

The shaft outer tube 111 and the shaft inner tube 112 are formed from a material or materials which are flexible and have such properties as to be able to transmit rotational power, acting from the proximal side, to the distal side. For example, a multilayer coil-shaped tubular body such as three-layer coil-shaped one in which winding direction is alternately changed (for example, clockwise, counterclockwise and clockwise), polyolefins such as polyethylene, polypropylene, polyamides, polyesters such as polyethylene terephthalate, fluoro-polymers such as ETFE, PEEK (polyether-ether ketone), polyimides, combinations thereof and the like in which a reinforcing member such as wire is embedded, can be used.

In addition, the material constituting the outermost sheath body 120 is not specifically restricted; for example, polyolefins such as polyethylene, polypropylene, polyamides, polyesters such as polyethylene terephthalate, fluoro-polymers such as ETFE, PEEK (polyether-ether ketone), polyimides and the like can be used suitably. In accordance with an exemplary embodiment, the outermost sheath body 120 may be formed from a plurality of materials, and a reinforcing member such as wire may be embedded therein.

A stirring unit 113 is provided at a distal portion of the shaft outer tube 111. The stirring unit 113 has base portions 113A fixed to a peripheral surface of the shaft outer tube 111, at two positions on the proximal side and the distal side, with a plurality of spiral portions 1138 arranged between the base portions 113A. The spiral portions 1138 are twisted in the same direction in regard of the axial direction, the positions of fixation to the base portions 113A are differing in the circumferential direction, and the positions in the axial direction where they are curved are differing, whereby the stirring unit 113 as a whole is formed in a shape of being bulged uniformly in the circumferential direction. When the shaft outer tube 111 is rotated, the stirring unit 113 is also rotated attendantly, whereby a thrombus in a blood vessel can be broken into fragments, or thrombus fragments can be stirred.

The spiral portions 1138 constituting the stirring unit 113 are composed of flexible metallic thin wires. Until the shaft main body 110 is inserted to a target site, the stirring unit 113 remains in the state of being accommodated in the inside of the outermost sheath body 120. After the shaft main body 110 is inserted to the target site, the proximal side of the outermost sheath body 120 is slid proximally, whereby the stirring unit 113 is exposed to the outside of the outermost sheath body 120, and is expanded into a shape as depicted in FIG. 7. Therefore, the spiral portions 1138 are desirably formed from a material that has a shape memory property. For example, shape memory alloys to which a shape memory effect and/or superelasticity is imparted by a heat treatment, stainless steel and the like can be suitably used as a material for the spiral portions 1136. As the shape memory alloy, those based on Ni—Ti, Cu—Al—Ni or Cu—Zn—Al and combinations thereof are preferably used.

The rotary drive unit 130 has a driving motor 131, and a gear portion 132 interconnecting the driving motor 131 with the shaft outer tube 111 of the shaft main body 110. With the driving motor 131 rotated, the shaft outer tube 111 can be rotated in the circumferential direction. In this exemplary embodiment, the shaft outer tube 111 is driven by the driving motor 131 so as to rotate alternately in positive and negative two directions in the circumferential direction. With the shaft outer tube 111 rotated alternately in the positive and negative two directions, blood flow can be alternately set in opposite directions.

The shaft outer tube 111 is formed in the vicinity of a distal portion thereof with a slot-shaped opening 160 elongated along the axial direction, through which the inside and the outside of the shaft outer tube 111 communicate with each other. The shaft outer tube 111 is provided at a distal portion thereof with a cylindrical contact portion 161 such as to plug up the hollow inside, whereby the distal portion of the shaft outer tube 111 is closed. A proximal surface of the contact portion 161 is a contact surface 161A facing a distal surface of the shaft inner tube 112. The contact surface 161A is located on the distal side as compared to a distal-side end portion of the opening 160 of the shaft outer tube 111. The contact portion 161 is formed from stainless steel or the like.

The shaft inner tube 112 has a distal-side end face located at the position of, or at a position on the proximal side as compared to, a proximal-side end portion of the opening 160 of the shaft outer tube 111. The shaft inner tube 112 is provided at a distal-side end portion thereof with a cutting unit 162 in the hollow inside. The cutting unit 162 is composed of a metallic thin sheet, has a width corresponding to the diameter of the shaft inner tube 112, and is formed on the distal side thereof with a sharp blade 162A.

As depicted in FIG. 9, a distal-side end face of the blade 162A and a distal-side end face of the shaft inner tube 112 are disposed with no step therebetween. Therefore, when the distal surface of the shaft inner tube 112 makes contact with the contact surface 161A of the contact portion 161, the blade 162A also makes contact with the contact surface 161A. The shaft inner tube 112 is configured to be reciprocatable in the axial direction relative to the shaft outer tube 111, at least from the position depicted in FIG. 9 to a position where it makes contact with the contact surface 161A of the contact portion 161. The distal portion of the shaft inner tube 112 may be thinner than the thickness (the thickness obtained by subtracting the inside diameter of the inner tube from the outside diameter of the inner tube) of other portions (than the distal portion) of the shaft inner tube 112, and may have a thinness comparable to that of the blade 162A of the cutting unit 162.

The shaft outer tube 111 and the shaft inner tube 112 are disposed coaxially, and the shaft outer tube 111 can be reciprocated along the circumferential direction by the rotary drive unit 130. It is to be noted, however, that the shaft outer tube 111 is not limited to the one that is reciprocated, but may be one that is rotated in one direction. The cutting unit 162 is disposed in such a manner as to bisect the cross-sectional shape of the hollow inside of the shaft inner tube 112.

Now, a method of using the medical device 10 and the removing device 100 according to this embodiment will be described below, taking as an example a case of removing a thrombus present in a blood vessel by suction.

First, an introducer sheath (not depicted) is percutaneously inserted into a blood vessel on the upstream side (proximal side) as compared to a thrombus 300 in the blood vessel, and a guidewire 80 is inserted into the blood vessel through the introducer sheath. Next, the guidewire 80 is pushed forward until it reaches the distal side of the thrombus 300.

Subsequently, as depicted in FIG. 2, the medical device 10 with the restrictor 20 and the pressing shaft 40 accommodated in the sheath 30 is prepared. The expanding section 22 is disposed at a position near a distal-side end portion of the sheath tubular body 31 of the sheath 30, and is constrained in shape in a contracted state. The shaft section 23 is protruding proximally from the hub opening 35 of the hub 32.

Next, a proximal-side end portion of the guidewire 80 located outside of the body is inserted into the guidewire lumen 26 of the medical device 10, and, as depicted in FIG. 10A, the medical device 10 is advanced along the guidewire 80 until it reaches the distal side of the thrombus 300. Note that for causing the guidewire 80 to reach the distal side of the thrombus 300, a support catheter prepared separately may be used.

Figure 11A:
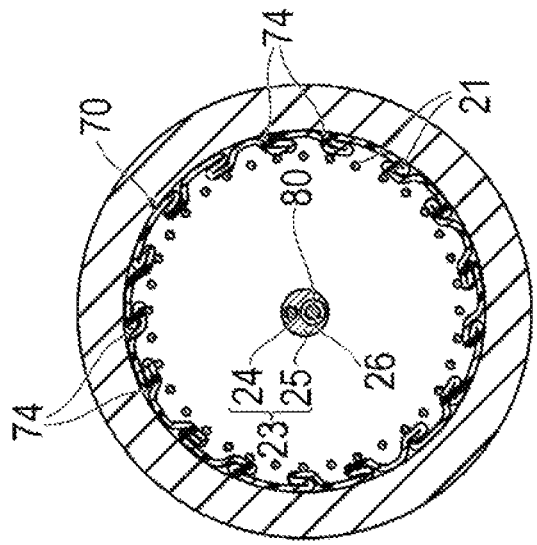
FIG. 11A is a sectional view taken along line XIA-XIA of FIG. 10.
Figure 11B:
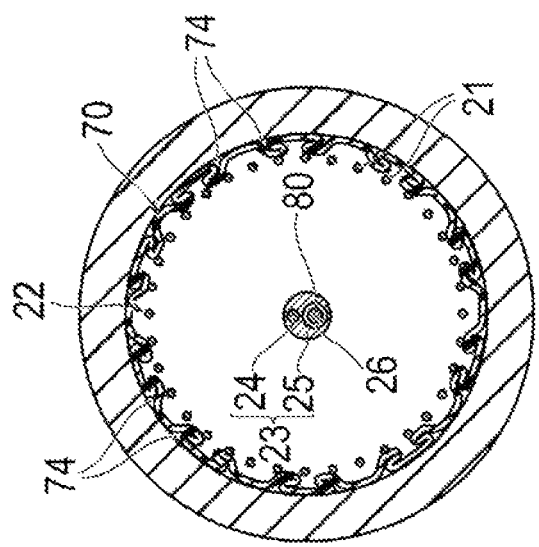
FIG. 11B is a sectional view taken along line XIB-XIB of FIG. 10.

Subsequently, while restricting movement of the pressing shaft 40 by hand, the sheath 30 is moved proximally. In this instance, a distal-side end portion of the pressing shaft 40 makes contact with a proximal-side end portion of the proximal-side connection portion 60 or the guidewire tubular body 25, whereby movement of the expanding section 22 and the cover section 70 is restricted. Therefore, with the sheath 30 moved proximally, the expanding section 22 and the cover section 70 are released out of the sheath tubular body 31. As a result, as depicted in FIGS. 10B and 11, while the distal-side connection portion 50 is moved closer to the proximal-side connection portion 60, the expanding section 22 expands to an optimum size by its own restoring force, to make contact with an inner wall surface of the blood vessel. Further, the cover section 70 is pressed against, and brought into contact with, the inner wall surface of the blood vessel by the expanding section 22. The expanding section 22 expands by its own restoring force, according to the inside diameter and the shape of the blood vessel, to make close contact with the inner wall surface of the blood vessel. Since the expanding section 22 is formed in a mesh-like form, the expanding section can be firmly fixed onto the inner wall surface of the blood vessel. The cover section 70 has the folded-back portions 74 pushed and spread while being stretched by the expanding section 22 according to the inside diameter and the shape of the blood vessel, and is pressed against, and brought into contact with, the inner wall surface of the blood vessel by the expanding section 22. Note that even if the folded-back portions 74 yet folded back remain in the state where the cover section 70 is in contact with the inner wall surface of the blood vessel, the cover section 70 is pressed against the inner wall surface of the blood vessel by the expanding section 22, and, therefore, no gap is generated between the cover section 70 and the blood vessel. In addition, since the plurality of folded-back portions 74 provided in the cover section 70 are formed to be short and intermittent in the axial direction, minute gaps generated between the folded-back portions 74 and the inner wall surface of the blood vessel, as depicted in FIGS. 11A and 11B, are also formed to be intermittent in the axial direction, and are not formed to be continuous in the axial direction of the cover section 70. For this reason, flow of blood can be effectively restrained by the cover section 70. Although the cover section 70 is more easily slid on the inner wall surface of the blood vessel than the expanding section 22, sliding of the cover section 70 relative to the blood vessel does not matter, since the expanding section 22 not covered by the cover section 70 is firmly fixed to the blood vessel. Thereafter, as depicted in FIG. 12A, the sheath 30 and the pressing shaft 40 are withdrawn to the outside of the body, leaving the restrictor 20 inside the body.

When the expanding section 22 and the cover section 70 make close contact with the inner wall surface of the blood vessel, the blood flow in the blood vessel is blocked or reduced, so that blood stagnates.

Figure 13A:
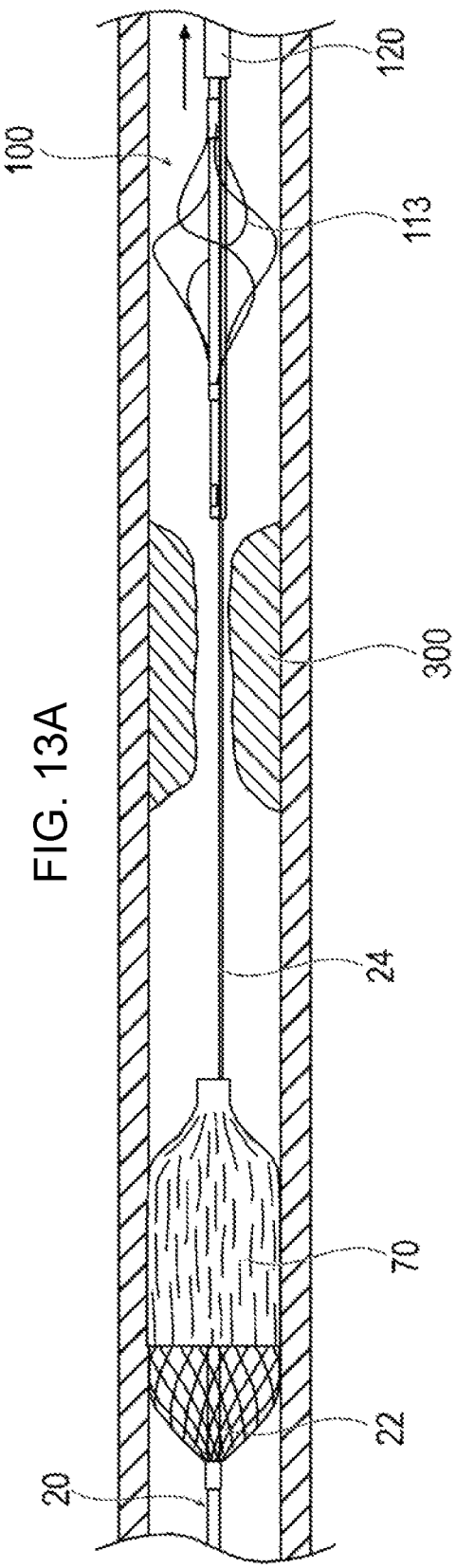
FIGS. 13A and 13B depict sectional views depicting a state inside a blood vessel, where

Next, the removing device 100 in the state in which a distal portion of the shaft main body 110 including the stirring unit 113 is accommodated in the outermost sheath body 120 is prepared, and a proximal-side end portion of the wire portion 24 is inserted into the second guidewire lumen 171 of the removing device 100. Thereafter, as depicted in FIG. 12B, with the wire portion 24 as a guide, the removing device 100 is inserted to the proximal side of the thrombus 300. Thereafter, the outermost sheath body 120 is moved proximally, whereon the stirring unit 113 is spread in the blood vessel, as depicted in FIG. 13A.

Subsequently, by utilizing the outermost sheath body 120, the shaft inner tube 112 or the second guidewire lumen 171 (see FIG. 8), a thrombolytic agent is injected into the vicinity of the thrombus 300 in the blood vessel. In this instance, since the blood flow in the region in which the thrombus is formed is restricted (blocked or reduced), the thrombolytic agent is kept in a high concentration, and the thrombolytic agent produces a high effect. Note that the thrombolytic agent may not necessarily be used.

Next, in the state in which the stirring unit 113 has been advanced into the vicinity of the thrombus 300, the shaft outer tube 111 is rotated by the rotary drive unit 130, whereon the stirring unit 113 is also rotated attendantly, whereby the thrombus 300 in the state of being secured in the blood vessel is broken into fragments.

Figure 13B:
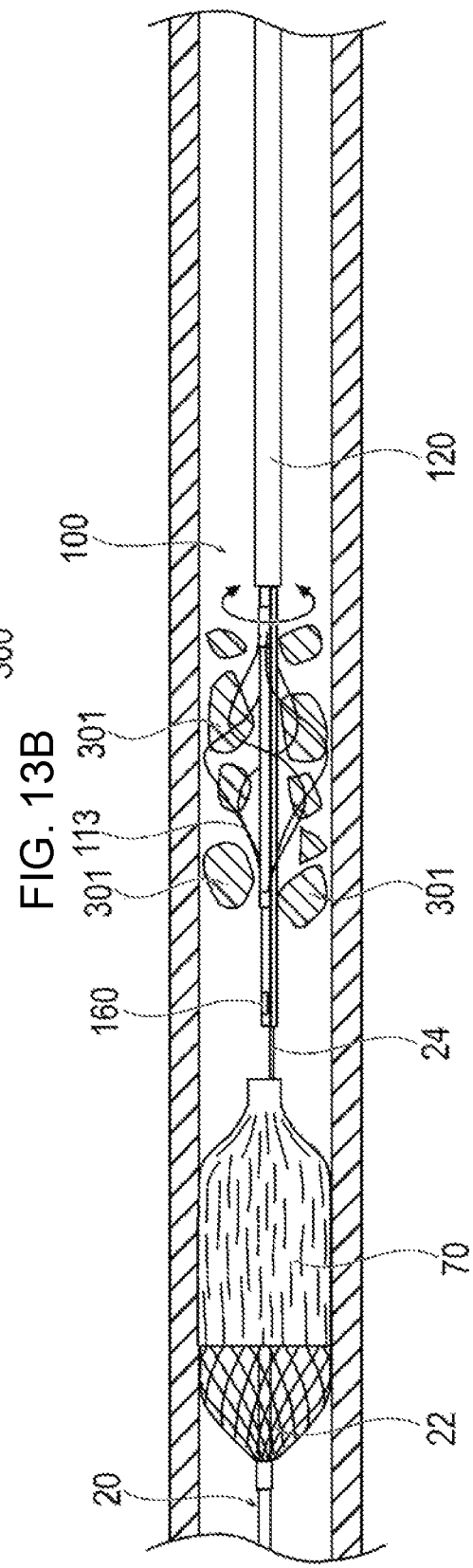

Since the flow of blood is being restricted by the medical device 10, as depicted in FIG. 13B, continuing the rotation of the stirring unit 113 causes the thrombus 300 secured in the blood vessel to be as a whole broken into fragments, and the fragments of the thrombus 301 are in a floating state, without undergoing precipitation or the like in the blood vessel in which a stagnating condition is kept.

Figure 14:
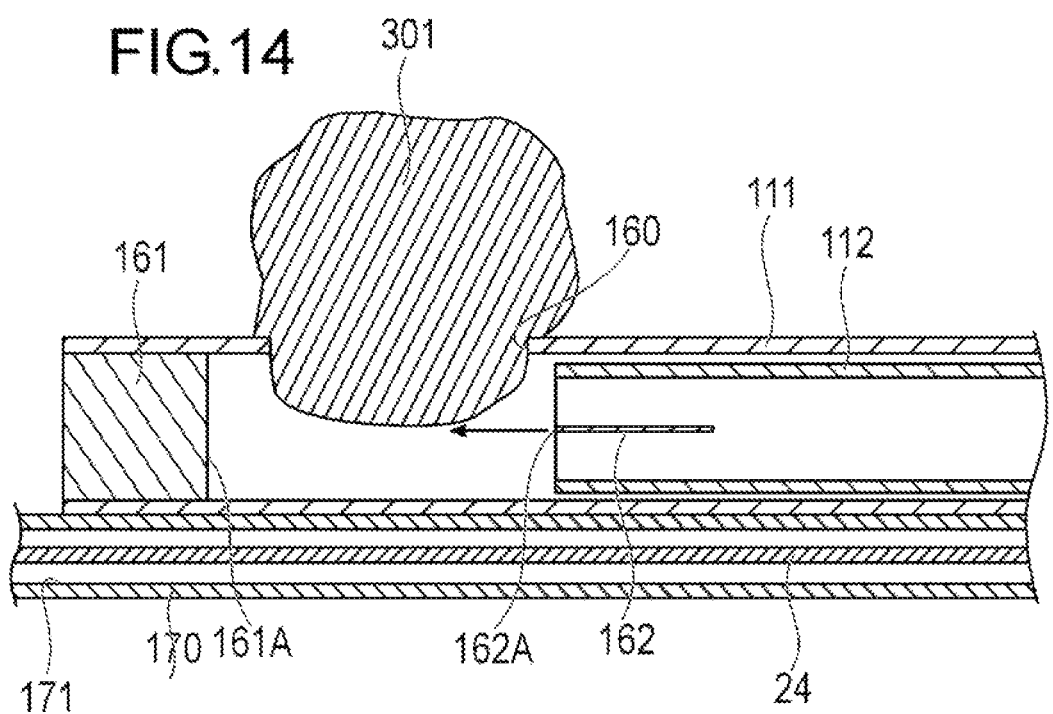
FIG. 14 is an enlarged sectional view of a distal portion of the removing device, depicting a state in which the thrombus fragments are sucked to an opening portion of an outer tube.

Subsequently, a pusher of the syringe 150 (see FIG. 7) is pulled to establish a negative pressure state in the hollow inside of the shaft inner tube 112. Since a distal-side end portion of the shaft inner tube 112 communicates with the hollow inside of the shaft outer tube 111 and, further, the shaft outer tube 111 communicates with the exterior of the shaft main body 110 through the opening 160, a suction force is generated at the opening 160 and applied to the exterior of the shaft main body 110, to draw the fragments of the thrombus 301 floating in the blood vessel. As depicted in FIG. 14, the thrombus 301 drawn to the opening 160 partly enters the hollow inside of the shaft outer tube 111.

Figure 15:
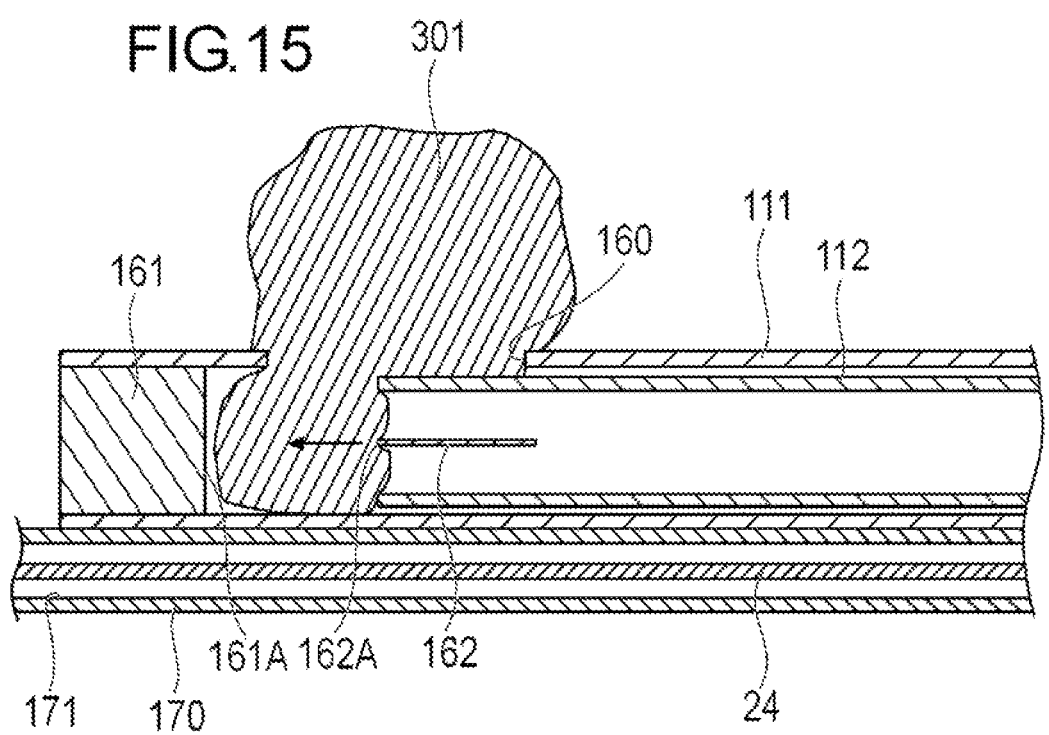
FIG. 15 is an enlarged sectional view of the distal portion of the removing device, depicting a process in which the thrombus sucked to the opening portion of the outer tube is cut off by an inner tube.

After the pusher of the syringe 150 is pulled, the shaft inner tube 112 is moved in the axial direction relative to the shaft outer tube 111. When the shaft inner tube 112 is moved toward the distal side of the shaft outer tube 111, namely, toward the side for approaching the contact portion 161 from a state in which the shaft inner tube 112 is located on the proximal side as compared to the opening 160, a part of the thrombus 301 having entered the hollow inside of the shaft outer tube 111 via the opening 160 is gradually cut off while being compressed by the distal surface of the shaft inner tube 112, as illustrated in FIG. 15.

Figure 16:
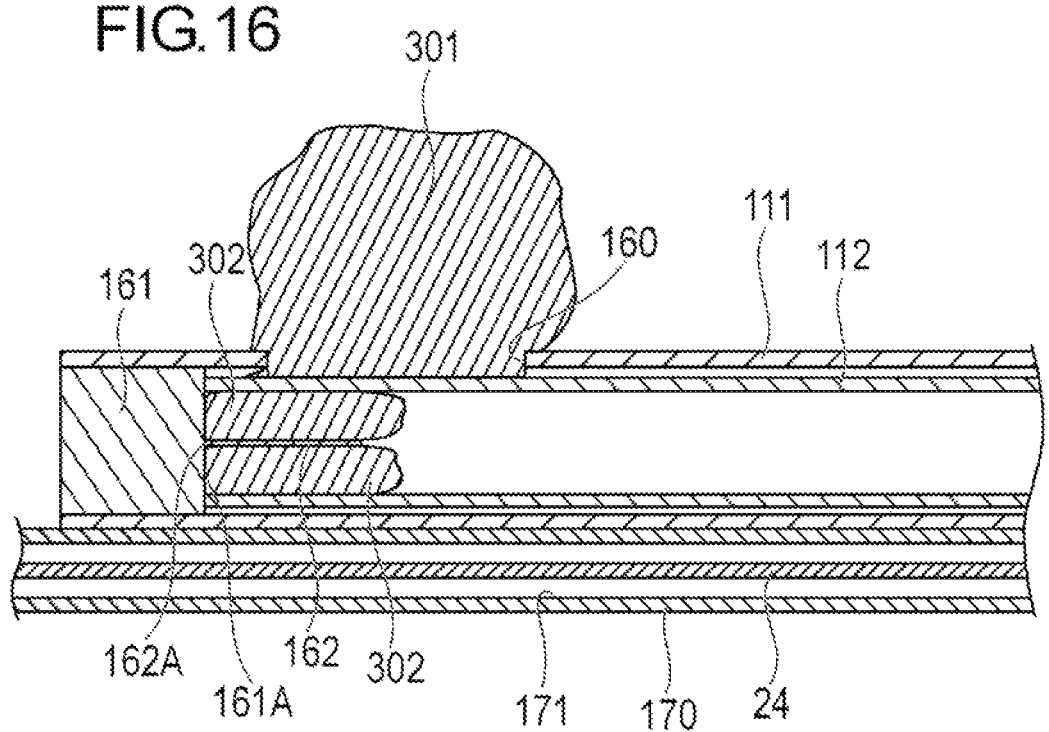
FIG. 16 is an enlarged sectional view of the distal portion of the removing device, depicting a state in which the thrombus cut off by the inner tube is cut by a cutting unit.

When the shaft inner tube 112 is moved until the distal surface of the shaft inner tube 112 comes into contact with the contact surface 161A of the contact portion 161, the cut-off thrombus 302 is neatly accommodated in the hollow inside of the shaft inner tube 112, as depicted in FIG. 16. In this instance, the thrombus 302 is cut in two by the blade 162A of the cutting unit 162 provided at a distal portion of the shaft inner tube 112. With the shaft inner tube 112 making contact with the contact surface 161A of the contact portion 161, the blade 162A also makes contact with the contact surface 161A, and the thrombus 302 cut off in the hollow inside of the shaft outer tube 111 is cut by the blade 162A while being pressed against the contact section 161. Therefore, the cut-off thrombus 302 can be cut assuredly, to be smaller than the inside diameter of the shaft inner tube 112. As a result, the cut-off thrombus 302 can be restrained from clogging in the hollow inside of the shaft inner tube 112.

Figure 17:
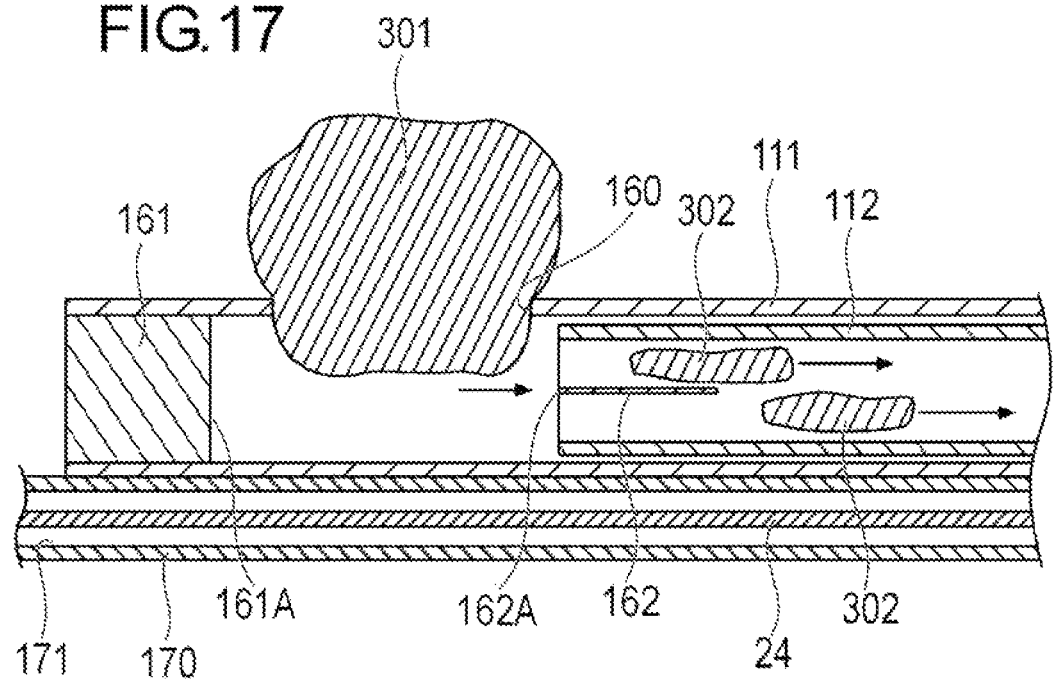
FIG. 17 is an enlarged sectional view of the distal portion of the removing device, depicting a process in which the thrombus cut by the cutting unit is sucked toward the proximal side of the inner tube.

Since the hollow inside of the shaft inner tube 112 is continuedly kept in the negative pressure state by the syringe 150, the cut-off thrombus 302 is gradually moved proximally in the hollow inside of the shaft inner tube 112, as depicted in FIG. 17. In addition, with the shaft inner tube 112 moved proximally parting from the contact portion 161, the opening 160 is again opened, and the thrombus 301 is sucked and enters the hollow inside of the shaft outer tube 111. Therefore, with the shaft inner tube 112 repeatedly reciprocated in the axial direction, the thrombus 301 can be sucked continuedly while being cut into minute pieces.

While the fragments of the thrombus 301 are being sucked by the shaft main body 110, the rotating operation of the shaft outer tube 111 is desirably continued. With the shaft outer tube 111 rotating, a vortex flow is generated in the blood in the blood vessel, and the thrombus 301 is liable to be collected in the vicinity of the center of rotation, namely, the vicinity of the center in the radial direction of the blood vessel, so that the thrombus 301 can be easily sucked via the opening 160. In addition, the vortex flow generated in the vicinity of the opening 160 also influences the flow in the hollow inside of the shaft inner tube 112, whereby a swirling flow of vortex is generated also in the inside of the shaft inner tube 112. As a result, flow resistance in regard of the axial direction is reduced in the inside of the shaft inner tube 112, and the cut thrombus 302 can be sucked relatively smoothly.

While the shaft outer tube 111 is rotated and the shaft inner tube 112 is reciprocated in the axial direction relative to the shaft outer tube 111 during suction of the thrombus 301 in this embodiment, other motions may be added. For example, where the shaft inner tube 112 is put into a different rotating motion (a rotation with the rotating direction reversed or a rotation in the same direction but at a different rotating speed) from that of the shaft outer tube 111, the thrombus 301 sucked to the opening 160 can thereby be cut off more reliably and be guided into the hollow inside of the shaft outer tube 111. In addition, where a reciprocating motion of the shaft outer tube 111 is added, the thrombus 300 in a wider range can thereby be broken into fragments and stirred.

In this embodiment, since the flow of blood is restricted by the medical device 10, the fragments of the thrombus 301 float in the stagnating blood, so that the thrombus 301 can be efficiently sucked through the opening 160 and removed from the inside of the blood vessel, without flowing to other part. In addition, when blood is flowing, a strong suction force is needed; in this embodiment, however, the blood flow is restrained, so that a suction force can be allowed to act relatively easily, and the thrombus 301 can be sucked effectively.

In accordance with an exemplary embodiment, a configuration may be adopted in which as depicted in FIG. 18A, at the time of suction of the thrombus 301, the removing device 100 is pressed against the cover section 70 to cause a proximal portion of the cover section 70 to be recessed, for example, and the thrombus 301 adhering to the cover section 70 can be sucked through the opening 160.

After the suction of the thrombus 301 is completed, the reciprocation and rotating motion of the shaft outer tube 111 and the shaft inner tube 112 are stopped, and the outermost sheath body 120 is moved in the axial direction to accommodate the stirring unit 113, as depicted in FIG. 18B. Thereafter, as depicted in FIG. 19A, the removing device 100 is withdrawn out of the blood vessel, leaving the restrictor 20 in the blood vessel.

Figure 21:
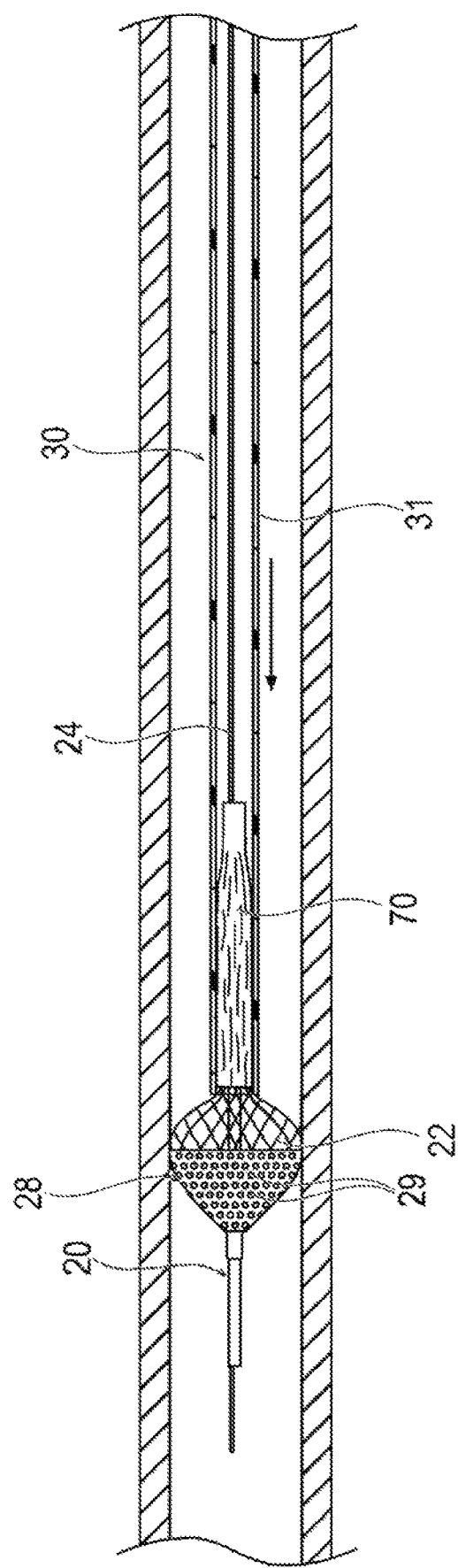
FIG. 21 is a sectional view depicting a modification of the medical device.

Next, a proximal-side end portion of the wire portion 24 is inserted into the sheath 30, and the sheath 30 is inserted into the blood vessel along the wire portion 24, to reach the vicinity of the expanding section 22 and the cover section 70. Subsequently, as depicted in FIG. 19B, while a proximal end portion of the wire portion 24 is grasped and movement thereof in the axial direction is restrained, the sheath 30 is pushed in, and the cover section 70 is accommodated into the inside of the sheath 30 while being reduced in diameter. When the cover section 70 is accommodated in the inside of the sheath 30 and the expanding section 22 comes into the state of making contact with the blood vessel, the thrombus 301 left in the blood vessel without being sucked may start flowing downstream in the blood vessel, but this thrombus 301 can be collected by the mesh-formed expanding section 22. The thrombus 301 may be caught on the outer surface side of the expanding section 22, and may be caught on the inner surface side of the expanding section 22. Particularly, at a part near the distal-side connection portion 50 of the expanding section 22, the diameter is small and the mesh openings are minute, so that small pieces of thrombus 301 can also collected effectively. Note that as in a modification depicted in FIG. 21, a separate filter 28 having a plurality of holes 29 may be provided at this part, for collecting the thrombus 301 after the recovery of the cover section 70 into the sheath 30.

In addition, the expanding section 22 may be moved proximally, in the state in which the cover section 70 has been recovered into the sheath 30 and the expanding section 22 is in contact with the blood vessel. By this, the thrombus 301 adhering to the inner wall surface of the blood vessel can be adhered to the mesh-formed expanding section 22 and be thereby collected.

Figure 20:
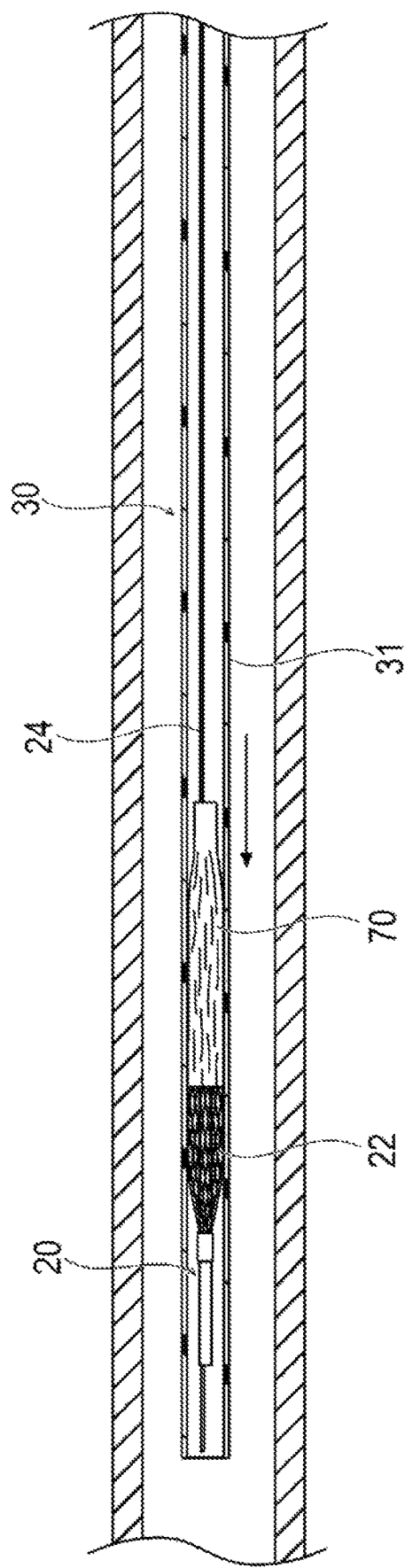
FIG. 20 is a sectional view depicting a state inside a blood vessel when the expanding section is accommodated in the sheath.

Thereafter, as depicted in FIG. 20, while a proximal-side end portion of the wire portion 24 is grasped and movement thereof in the axial direction is restrained, the sheath 30 is pushed in further, whereby the expanding section 22 is accommodated into the inside of the sheath 30 together with the collected thrombus 301 while being reduced in diameter. Thereafter, the restrictor 20 is withdrawn out of the blood vessel together with the sheath 30, whereby the treatment is completed.

As has been described above, the medical device 10 according to this embodiment is a medical device 10 to be inserted into a body lumen for restricting flow within the body lumen, the medical device 10 including: the elongated shaft section 23; the expanding section 22 that is an elastically deformable tubular body provided with a plurality of openings 21A and includes a central portion greater in outside diameter than end portions on both sides of the tubular body in a natural state in which no external force is applied, with the shaft section 23 being coupled to at least one of the end portions; the flexibly deformable tubular cover section 70 that is coupled to an end portion on a proximal side of the expanding section 22, surrounds an outer periphery of the expanding section 22 on the proximal side, but does not surround, and externally expose, an outer periphery of the expanding section 22 on a distal side; and the sheath 30 capable of accommodating the expanding section 22 and the cover section 70 in a diameter-reduced state. In the medical device 10 configured in this way, when the expanding section 22 and the cover section 70 are released out of the sheath 30, the expanding section 22 expands by its own elastic force in conformity with the shape of the body lumen, the cover section 70 is pressed against the body lumen by the expanding section 22, and that part of the expanding section 22 which is not surrounded by the cover section 70 makes direct contact with the body lumen and is fixed. Therefore, by the expanding section 22 that expands by its own elastic force, the range of inside diameter of the body lumen that is applicable is widened, the flow within the body lumen can be effectively restricted by the cover section 70, and a property for suction of a substance from the inside of the body lumen can be enhanced. In addition, with the medical device 10 inserted from the upstream side in regard of blood flow, the cover section 70 surrounds the upstream side (proximal side) of the expanding section 22. Therefore, the cover section 70 receives the flow within the body lumen, not by its inner surface which is recessed in shape but by its outer surface. Accordingly, the cover section 70 can restrict the flow within the body lumen by its outer surface, and can capture the substance such as a thrombus. For this reason, the expanding section 22 located on the downstream side (distal side) of the cover section 70 functions as a back-up for the cover section 70, and holds the cover section 70 favorably, whereby the function of the cover section 70 can be displayed to the utmost degree.

In addition, the maximum-outside-diameter portion the expanding section 22 in its expanded state is greater than the maximum-outside-diameter portion of the cover section 70 in its expanded state. Accordingly, by effectively utilizing the expanding section 22 higher in frictional resistance than the cover section 70, the medical device 10 can be fixed to the body lumen favorably.

In accordance with an exemplary embodiment, on the distal side as compared to a proximal-side end portion of the cover section 70 that is coupled to the expanding section 22, the cover section 70 is not coupled to the expanding section 22 and is movable independently of the expanding section 22. As a result, deformation of the expanding section 22 is not obstructed by the cover section 70, the expanding section 22 can be effectively expanded and contracted, and the medical device 10 can be favorably fixed to the body lumen.

In addition, the expanding section 22 has one of its end portions fixed to the shaft section 23, and has the other of its end portions connected to the shaft section 23 in such a manner as to be movable in the axial direction relative to the shaft section 23. As a result, the length in the axial direction of the expanding section 22 can be varied largely, and, attendantly, variation in its outside diameter is less liable to be hindered, and the expanding section 22 can be deformed largely. Therefore, the medical device 10 can be applied to a body lumen, even if the inside diameter of the body lumen is large, for example.

In accordance with an exemplary embodiment, the proximal side of the expanding section 22 to which the cover section 70 is coupled is configured to be located on the upstream side in the body lumen into which the medical device 10 is inserted, which helps ensures that the cover section 70 would not be turned up from the expanding section 22 by flow of blood (liquid) within the body lumen, so that the cover section 70 can be maintained on the outside of the expanding section 22 in a favorable manner.

In addition, the medical device 10 has the pressing shaft 40 which is a tubular body accommodated in the sheath 30 and penetrated by the shaft section 23, is formed to have such an inside diameter that the expanding section 22 and the cover section 70 in the sheath 30 cannot pass therethrough, and pushes the expanding section 22 and the cover section 70 out of the sheath 30. By utilizing the pressing shaft 40, therefore, the expanding section 22 and the cover section 70 can be easily pushed out of the sheath 30.

In accordance with an exemplary embodiment, the present disclosure provides also a treatment method for removing an object generated at a lesion part in a body lumen by suction by use of the aforementioned medical device. The method includes: (i) a step of pushing out the expanding section from the sheath to a downstream side of the lesion part in the body lumen, with the side of being surrounded by the cover section on the upstream side, to allow the expanding section to expand by its own elastic force to press the cover section against the body lumen, and to cause an expanding section's part not surrounded by the cover section to make direct contact with the body lumen and be fixed to the body lumen; (ii) a step of breaking the object generated at the lesion part in the body lumen into fragments; (iii) a step of inserting into the body lumen a device provided with a suction port and capable of sucking, and sucking the object fragments; (iv) a step of contracting the expanding section and the cover section; and (v) a step of withdrawing the medical device from the inside of the body lumen. In the treatment method configured in this way, when the expanding section and the cover section are released out of the sheath of the medical device, the expanding section expands by its own elastic force in conformity with the shape of the body lumen, the cover section is pressed against the body lumen by the expanding section, and the cover section's part not surrounded by the expanding section makes direct contact with the body lumen. Therefore, owing to the expanding section that expands by its own elastic force, the range of inside diameter of the body lumen applicable is widened, and the flow within the body lumen can be effectively restricted by the cover section. Accordingly, the fragments of the object (thrombus) float in the stagnating blood, and the object fragments can be efficiently sucked through the opening and be removed from the inside of the body lumen, without flowing to other part. In addition, although a strong suction force is needed when blood is flowing, the restraint of blood flow by the cover section ensures that the suction force is allowed to act easily, and the object can be sucked more effectively.

In addition, in the aforementioned treatment method, a step may be provided in which before insertion of the cover section into the sheath, the cover section is formed with folded-back portions inclined at an angle relative to the axial direction, whereby a plurality of folded-back portions inclined relative to the axial direction are provided in the circumferential direction, and, at the time inserting or releasing the cover section into or out of the sheath, the cover section is inserted or released while being twisted. By this, the resistance at the time of inserting the cover section into the sheath and the resistance at the time of releasing the cover section out of the sheath can be reduced.

Note that the present disclosure is not limited only to the aforementioned embodiment, and various modifications can be made by a person skilled in the art within the technical thought of the present disclosure. For example, a structure in which an affected area is accessed by the medical device from the upstream side of the affected area is adopted in this embodiment, a structure in which the affected area is accessed from the downstream side of the affected area may be adopted. In this case, since the cover section should be located on the upstream side, in regard of blood flow, of the expanding section 22, the cover section is configured not to cover the proximal side of the expanding section 22 but to cover the distal side of the expanding section 22.

In accordance with an exemplary embodiment, the body lumen into which the medical device 10 is inserted is not limited to a blood vessel, but may be, for example, a vessel, a ureter, a bilary duct, an ovarian duct, or a hepatic duct. Besides, the removing device is not restricted to the aforementioned configuration.

In addition, the expanding section 22 and the cover section 70 have their end portions in the axial direction formed in a tapered shape, the end portions may not necessarily be formed in a tapered shape.

In accordance with an exemplary embodiment, at least part of the distal-side connection portion 50, the proximal-side connection portion 60 and the wires 21 may be formed from a material in which a radiopaque material is contained. For example, part of the plurality of wires 21 may be formed from a material in which a radiopaque material is contained, which helps ensure that position can be accurately grasped under radioscopy, and a treatment can be performed easily. Preferable examples of the radiopaque material include gold, platinum, platinum-indium alloys, silver, stainless steel, molybdenum, tungsten, tantalum, palladium and their alloys.

The detailed description above describes a medical device and a treatment method to be used for removing an object present in a body lumen. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device to be inserted into a body lumen for restricting flow within the body lumen, the medical device comprising:
   an elongated shaft section possessing a proximal end and a distal end, the distal end configured to be inserted into the body lumen;
   an expanding section that is an elastically deformable tubular body including a plurality of openings, the expanding section including a central portion greater in outer diameter than end portions on both sides of the tubular body in a natural state in which no external force is applied, with the elongated shaft section being coupled to at least one of the end portions of the expanding section;
   a flexibly deformable tubular cover section configured to prevent a fluid flow and coupled to an end portion on a proximal side of the expanding section, surrounds an outer periphery of the expanding section on the proximal side, but does not surround, and externally exposes, an outer periphery of the expanding section on a distal side, and wherein the flexibly deformable tubular cover section is formed from a thin film to cover the proximal side of the expanding section, and wherein a maximum outer diameter portion of the expanding section that is not covered by the cover section in an expanded state is greater than a maximum outer diameter of the covered section in the expanded state, and wherein the maximum outer diameter portion of the expanding section that is not covered by the cover section is distal to the central portion of the expanding section;
   the cover section comprising a cover proximal portion secured to an outer peripheral surface of a proximal-side connection portion, a cover taper portion tapering toward a distal side of the cover section from the cover proximal portion, and a cover distal portion tapering to a distal end of the cover section, wherein the cover taper portion has an inner diameter and an outer diameter increasing in a taper towards the distal side of the cover section from the cover proximal portion, and the cover distal portion having an inner diameter and an outer diameter increasing in a taper to the distal end of the cover section, and wherein a position where the expanding section and the cover section make contact with each other in an expanded state is different from a position where the expanding section and the cover section make contact with each other in a contracted state; and
   a sheath capable of accommodating the expanding section and the cover section in a diameter-reduced state.

2. The medical device according to claim 1, wherein the cover section is not coupled to the expanding section, and is movable independently of the expanding section, on a more distal side than a proximal-side end portion coupled to the expanding section.

3. The medical device according to claim 1, wherein the expanding section has one of the end portions fixed to the shaft section, and has the other of the end portions connected to the shaft section in such a manner as to be movable in an axial direction relative to the shaft section.

4. The medical device according to claim 1, wherein the cover section has a folded-back portion which is slanted relative to the axial direction when contracted or when expanded.

5. A treatment method for removing an object generated at a lesion part in a body lumen by suction by use of the medical device according to claim 1, the treatment method comprising:
pushing out the expanding section from the sheath to a downstream side of the lesion part in the body lumen, with the side of the expanding section being surrounded by the cover section on an upstream side, to allow the expanding section to expand by its own elastic force to press the cover section against the body lumen, and to cause an expanding section's part not surrounded by the cover section to make direct contact with the body lumen and be fixed to the body lumen;
breaking the object generated at the lesion part in the body lumen into fragments; and
inserting into the body lumen a device provided with a suction port; and
suctioning the fragments of the object.

6. The treatment method according to claim 5, further comprising:
contracting the expanding section and the cover section; and
withdrawing the medical device from the inside of the body lumen.

7. The medical device according to claim 1, wherein the expanding section is a mesh.

8. The medical device according to claim 1, wherein the expanding portion is a plurality of flexibly deformable wires knitted in a mesh form.

9. The medical device according to claim 8, wherein an outer diameter of the expanding section varies attended by a variation in an intersection angle of the plurality of flexible deformable wires knitted in the mesh form and wherein the expanding section decreases in length in an axial direction when the outer diameter of the expanding diameter increases.

10. A medical device configured to be inserted into a body lumen for restricting flow within the body lumen, the medical device comprising:
an elongated shaft section possessing a proximal end and a distal end, the distal end configured to be inserted into the body lumen;
an expanding section that is an elastically deformable tubular body including a plurality of openings and is coupled to the elongated shaft section;
a flexibly deformable tubular cover section configured to prevent a fluid flow and coupled to an end portion on a proximal side of the expanding section, and wherein the flexibly deformable tubular cover surrounds the proximal side of the expanding section and exposes a distal side of the expanding section, and wherein a maximum outer diameter portion of the expanding section that is not covered by the cover section has in an expanded state is greater than a maximum outer diameter of the covered section in the expanded state, and wherein the maximum outer diameter portion of the expanding section that is not covered by the cover section is distal to a central portion of the expanding section, and wherein the flexibly deformable tubular cover section is formed from a thin film to cover the proximal side of the expanding section; and
wherein cover section comprises a cover proximal portion secured to an outer peripheral surface of a proximal-side connection portion, a cover taper portion tapering toward a distal side of the cover section from the cover proximal portion, and a cover distal portion tapering to a distal end of the cover section, wherein the cover taper portion has an inner diameter and an outer diameter increasing in a taper towards the distal side of the cover section from the cover proximal portion, and the cover distal portion having an inner diameter and an outer diameter increasing in a taper to the distal end of the cover section, and wherein a distal-side end portion of the cover section is configured to move proximally relative to the expanding section at a time of transition from the expanded state into a contracted state, and the distal-side end portion of the cover section is configured to move distally relative to the expanding section at the time of transition from the contracted state into the expanded state.

11. The medical device according to claim 10, wherein the central portion of the expanding section is greater in outer diameter than end portions on both sides of the tubular body in a natural state in which no external force is applied.

12. The medical device according to claim 11, wherein the shaft section is coupled to at least one end portion of the expanding section.

13. The medical device according to claim 10, wherein the flexibly deformable tubular cover section does not surround, and externally exposes, an outer periphery of the expanding section on a distal side.

14. The medical device according to claim 10, further comprising:
a sheath capable of accommodating the expanding section and the cover section in a diameter-reduced state.

15. The medical device according to claim 10, wherein the cover section is not coupled to the expanding section, and wherein the cover section is movable independently of the expanding section, on a more distal side than a proximal-side end portion coupled to the expanding section.

16. The medical device according to claim 10, wherein the expanding section has one of the end portions fixed to the shaft section, and has the other of the end portions connected to the shaft section in such a manner as to be movable in an axial direction relative to the shaft section.

17. A treatment method for removing an object generated at a lesion part in a body lumen by suction by use of the medical device according to claim 10, the treatment method comprising:
pushing out the expanding section from a sheath to a downstream side of the lesion part in the body lumen, with the side of the expanding section being surrounded by the cover section on an upstream side, to allow the expanding section to expand by its own elastic force to press the cover section against the body lumen, and to cause an expanding section's part not surrounded by the cover section to make direct contact with the body lumen and be fixed to the body lumen;
breaking the object generated at the lesion part in the body lumen into fragments;
inserting into the body lumen a device provided with a suction port; and
suctioning the fragments of the object.

18. The medical device according to claim 10, wherein the expanding section is a mesh.

19. A medical device to be inserted into a body lumen for restricting flow within the body lumen, the medical device comprising:

an elongated shaft section possessing a proximal end and a distal end, the distal end configured to be inserted into the body lumen;

an expanding section that is an elastically deformable tubular body including a plurality of openings, the expanding section including a central portion greater in outer diameter than end portions on both sides of the tubular body in a natural state in which no external force is applied, with the elongated shaft section being coupled to at least one of the end portions of the expanding section;

a flexibly deformable tubular cover section configured to prevent a fluid flow and coupled to an end portion on a proximal side of the expanding section, surrounds an outer periphery of the expanding section on the proximal side, but does not surround, and externally exposes, an outer periphery of the expanding section on a distal side, and wherein the flexibly deformable tubular cover section is formed from a thin film to cover the proximal side of the expanding section, and wherein a maximum outer diameter portion of the expanding section that is not covered by the cover section in an expanded state is greater than a maximum outer diameter of the covered section in the expanded state, and wherein the maximum outer diameter portion of the expanding section that is not covered by the cover section is distal to the central portion of the expanding section; and the cover section comprising a cover proximal portion secured to an outer peripheral surface of a proximal-side connection portion, a cover taper portion tapering toward a distal side of the cover section from the cover proximal portion, and a cover distal portion tapering to a distal end of the cover section, wherein the cover taper portion has an inner diameter and an outer diameter increasing in a taper towards the distal side of the cover section from the cover proximal portion, and the cover distal portion having an inner diameter and an outer diameter increasing in a taper to the distal end of the cover section, and wherein the inner and the outer diameters of the cover distal portion slightly increase, though not so largely as the inner and the outer diameters of the cover taper portion, toward the distal side from the cover taper portion.

20. The medical device according to claim 19, wherein the expanding portion is a plurality of flexibly deformable wires knitted in a mesh form, and an outer diameter of the expanding section varies attended by a variation in an intersection angle of the plurality of flexible deformable wires knitted in the mesh form and wherein the expanding section decreases in length in an axial direction when the outer diameter of the expanding diameter increases.

* * * * *